United States Patent [19]
Bratz et al.

[11] Patent Number: 5,723,413
[45] Date of Patent: Mar. 3, 1998

[54] SUBSTITUTED NAPHTHYRIDINES AND THEIR HERBICIDAL USE

[75] Inventors: Matthias Bratz, Speyer; Norbert Meyer, Ladenburg; Hartmann König, Limburgerhof; Helmut Walter, Obrigheim; Matthias Gerber, Limburgerhof; Karl-Otto Westphalen, Speyer, all of Germany

[73] Assignee: BASF Aktiengesellschaft, Ludwigshafen, Germany

[21] Appl. No.: 392,474

[22] Filed: Feb. 22, 1995

[30] Foreign Application Priority Data

Feb. 23, 1994 [DE] Germany ............... 44 05 712.1

[51] Int. Cl.$^6$ ............... A01N 43/40; C07D 471/04
[52] U.S. Cl. ............... 504/246; 546/122; 546/81; 504/245
[58] Field of Search ............... 546/122, 81; 514/300; 504/246, 245

[56] References Cited

U.S. PATENT DOCUMENTS

| | | | |
|---|---|---|---|
| 4,881,969 | 11/1989 | Saupe et al. | 71/94 |
| 5,034,399 | 7/1991 | Hubsch et al. | 514/300 |
| 5,059,240 | 10/1991 | Hagen et al. | 71/94 |

FOREIGN PATENT DOCUMENTS

| | | |
|---|---|---|
| 166 907 | 1/1986 | European Pat. Off. . |
| 227 932 | 11/1986 | European Pat. Off. . |
| 230 239 | 7/1987 | European Pat. Off. . |
| 326 331 | 8/1989 | European Pat. Off. . |
| 387 582 | 9/1990 | European Pat. Off. . |
| 410762 | 1/1991 | European Pat. Off. . |
| 414 386 | 2/1991 | European Pat. Off. . |
| 346208 | 4/1994 | European Pat. Off. . |
| 92/07468 | 5/1992 | WIPO . |

OTHER PUBLICATIONS

Chemical Abstracts, 1507$^2$; Abstract of Migliardi, Atti Acad. Sci. Torino, Classe Sci. Fis. Mat. Nat. 75I, pp. 548–551 (1940) 1944.

J. of Med. Chem., vol. 20, No. 6, 1977, Hawes et al., pp. 838–840.
Ind. J. of Chem., vol. 27B, Feb. 1988, pp. 200–202, Rao et al.
J. Ind. Chem., vol. LXIII, Apr. 1986, pp. 443–446, Reddy et al.
J. Chem. Soc. (C), 1966, pp. 315–320, Hawes et al.
Chem. Pharm. Bull., vol. 26, 1978, pp. 3242–3243, Higashino et al.
Yakugaku Zasshi, 1979, vol. 99, pp. 451–457.
J. of Med. Chem., vol. 20, No. 1, 1977, pp. 124–128, Gorecki et al.
Tetrahedron Letters, vol. 23, No. 50, pp. 5291–5294, 1982, Dietrich–Buchecker et al.
J. Heterocycl. Chem., vol. 23, 1986, pp. 689–693, Thummel et al.
Tetrahedron, vol. 36, pp. 2359–2407, Caluwe. 1980.
Nat. Acad. Sci. Letters, vol. 8, No. 1, 1985, pp. 18–21, Reddy et al.
J. Chem. Soc. (C), 1967, pp. 1564–1568, Hawes et al.
Rao et al., Collect. Czech. Chem. Comm., vol. 54, 1989, pp. 1716–1720.
Gorecki et al., J. Med. Chem., vol. 20, No. 1, 1977, pp. 124–128.

Primary Examiner—Bernard Dentz
Attorney, Agent, or Firm—Keil & Weinkauf

[57] ABSTRACT

Naphthyridines of the formula I $$\begin{array}{c}R^3 \quad R^4 \\ R^2 \diagup\!\!\!\diagdown\!\!\!\diagup\!\!\!\diagdown R^5 \\ R^1 \diagdown\!\!\!\diagup N \quad N \diagdown\!\!\!\diagup R^6\end{array} \quad I$$

where $R^1$ is an unsubstituted or substituted phenyl ring or heteroaromatic radical and $R^2$–$R^6$ are hydrogen, alkyl, alkenyl, cycloalkyl, haloalkyl, alkoxyalkyl, aminoalkyl, unsubstituted or substituted phenyl, benzyl, unsubstituted or substituted heteroaryl linked via a carbon, cyano, nitro, carboxyl, sulfonylmethyl, alkoxycarbonyl, carbamoyl, alkylcarbamoyl, dialkylcarbamoyl, alkanoyl, benzoyl, it being possible for $R^4$ and $R^5$ or $R^5$ and $R^6$ to be bonded by a methylene chain or by a CH=CH—CH=CH group.

16 Claims, No Drawings

SUBSTITUTED NAPHTHYRIDINES AND THEIR HERBICIDAL USE

The present invention relates to substituted naphthyridines of the general formula I

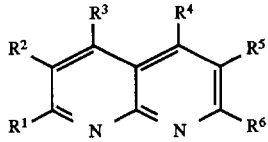

where the substituents have the following meanings:
$R^1$ is
(a) an unsubstituted or substituted five-membered heteroaromatic having one or two heteroatoms, selected from nitrogen, oxygen or sulfur, it also being possible for the heteroatom to be benzo-fused;
(b) an unsubstituted or substituted six-membered heteroaromatic containing one or two nitrogen atoms;
(c) phenyl substituted by one to four substituents selected from the group consisting of $C_1$-$C_8$-alkyl, $C_2$-$C_8$-alkenyl, $C_2$-$C_8$-alkynyl, $C_3$-$C_8$-cycloalkyl, phenyl, $C_1$-$C_5$-alkoxy, $C_1$-$C_5$-thioalkyl, a five- or six-membered saturated heterocycle, a five-or six-membered aromatic heterocycle, it being possible for all the abovementioned substituents in each case to be additionally mono-to trisubstituted themselves, hydroxyl, an $OC(O)R^{14}$ group, amino, an $NR^{15}R^{16}$ group, halogen, cyano, nitro, carboxyl, an $R^7SO_2$— group, —$C(O)R^8$, —$C(Y)R^9$, Y being oxygen or an $NR^{13}$ group, or —$C(VR^{10}WR^{11})R^{12}$, V and W independently of one another being O or S;
$R^7$ is $C_1$-$C_8$-alkyl, $C_3$-$C_8$-cycloalkyl, $C_1$-$C_8$-haloalkyl, $C_1$-$C_5$-alkoxy, phenyl, naphthyl, aryl($C_1$-$C_6$)-alkyl, heteroaryl, hydroxyl, amino, $C_1$-$C_8$-monoalkyl- or $C_1$-$C_8$-dialkylamino, $C_5$-$C_8$-cycloalkylamino;
$R^8$ is hydroxyl, amino, $C_1$-$C_8$-monoalkyl- or $C_1$-$C_8$-dialkylamino, $C_5$-$C_8$-cycloalkylamino, $C_1$-$C_6$-alkylthio, $C_1$-$C_8$-alkoxy;
$R^9$ is hydrogen, $C_1$-$C_8$-alkyl, $C_3$-$C_8$-cycloalkyl, $C_1$-$C_8$-haloalkyl, $C_1$-$C_4$-alkoxy ($C_1$-$C_6$)-alkyl, $C_1$-$C_8$-aminoalkyl, phenyl, aryl ($C_1$-$C_6$) -alkyl, heteroaryl;
$R^{10}$ and $R^{11}$ are $C_1$-$C_8$-alkyl, $C_1$-$C_6$-haloalkyl or $C_1$-$C_4$-alkoxy($C_1$-$C_6$)-alkyl, or $R^{10}$ and $R^{11}$ together form a di-, tri- or tetramethylene chain which is unsubstituted or substituted by one or two $C_1$-$C_8$-alkyl, $C_1$-$C_6$-haloalkyl, $C_1$-$C_4$-alkoxy($C_1$-$C_6$)-alkyl groups or by an oxo group;
$R^{12}$ is hydrogen, $C_1$-$C_8$-alkyl, $C_3$-$C_8$-cycloalkyl, $C_1$-$C_8$-haloalkyl, $C_1$-$C_4$-alkoxy($C_1$-$C_6$)-alkyl, $C_1$-$C_8$-aminoalkyl, phenyl, aryl($C_1$-$C_6$)-alkyl, heteroaryl;
$R^{13}$ is $C_1$-$C_8$-alkyl, $C_2$-$C_8$-alkenyl, $C_3$-$C_8$-cycloalkyl, $C_1$-$C_8$-haloalkyl, $C_1$-$C_4$-alkoxy($C_1$-$C_6$)-alkyl, $C_1$-$C_8$-aminoalkyl, phenyl, aryl($C_1$-$C_6$)-alkyl, heteroaryl, hydroxyl, unsubstituted or substituted $C_6$-$C_{10}$-aryloxy, unsubstituted or substituted $C_1$-$C_8$-alkoxy, amino, $C_1$-$C_8$-monoalkyl- or $C_1$-$C_8$-dialkylamino, $C_5$-$C_8$-cycloalkylamino, unsubstituted or substituted $C_6$-$C_{10}$-arylamino;
$R^{14}$ is $C_1$-$C_5$-alkyl, unsubstituted or substituted phenyl, $C_1$-$C_5$-alkoxy, $C_1$-$C_5$-haloalkoxy, benzyloxy, amino, alkylamino, dialkylamino, a saturated five- or six-membered heterocycle bonded via N, which can additionally contain a further heteroatom N or O; ;
$R^{15}$ is hydrogen, $C_1$-$C_5$-alkyl, unsubstituted or substituted phenyl;
$R^{16}$ is hydrogen, $C_1$-$C_5$-alkyl, unsubstituted or substituted phenyl, a —$C(O)R^{14}$ group or $R^{16}$ together with $R^{15}$ forms a four- or five-membered methylene chain which in turn can be substituted by one or two methyl groups and in which one methylene group can be replaced by oxygen;
(d) phenyl in which two directly adjacent positions are bonded to one another via a tri- or tetramethylene group which in turn can carry one to three $C_1$-$C_3$-alkyl, $C_1$-$C_2$-alkoxy and/or halogen substituents, and the other positions are unsubstituted or are substituted by one of the phenyl substituents mentioned under (c);
(e) phenyl which is bonded to $R^2$ via the ortho position to give a chain of one to four methylene groups or one to three methylene groups and one oxygen atom, it being possible for each methylene group to carry one or two $C_1$-$C_3$-alkyl radicals;
$R^2$-$R^6$ are hydrogen, $C_1$-$C_8$-alkyl, $C_2$-$C_8$-alkenyl, $C_3$-$C_8$-cycloalkyl, $C_1$-$C_8$-haloalkyl, $C_1$-$C_4$-alkoxy($C_1$-$C_6$)-alkyl, $C_1$-$C_8$-aminoalkyl, unsubstituted or substituted phenyl, benzyl, unsubstituted or substituted five- or six-membered heteroaryl linked via a carbon, cyano, nitro, carboxyl, sulfonylmethyl, $C_1$-$C_4$-alkoxycarbonyl, carbamoyl, $C_1$-$C_8$-alkylcarbamoyl, dialkylcarbamoyl, $C_1$-$C_4$-alkanoyl, benzoyl or $R^4$ and $R^5$ or $R^5$ and $R^6$ together form a $CH_2$—$(CH_2)_n$—$CH_2$ chain where n=1 to 3 or an unfused aromatic ring;
with the proviso that compounds having the following substituent combinations are excluded:
i) if $R^1$=phenyl and $R^3$-$R^6$=hydrogen,
  $R^2$ is not hydrogen, methyl, ethyl, n-propyl, phenyl or chlorine;
ii) if $R^1$=phenyl and $R^2$-$R^5$=hydrogen,
  $R^6$ is not phenyl or methyl;
iii) if $R^1$=phenyl and $R^2$-$R^4$ and $R^6$=hydrogen,
  $R^5$ is not phenyl or benzoyl;
iv) if $R^1$=phenyl, $R^2$-$R^4$=hydrogen and $R^6$=methyl,
  $R^5$ is not acetyl or ethoxycarbonyl;
v) if $R^1$=phenyl, $R^3$=chlorine, $R^2$, $R^4$ and $R^5$=hydrogen,
  $R^6$ is not methyl;
vi) if $R^1$=phenyl, $R^2$=cyano and $R^3$+$R^5$=hydrogen,
  $R^4$ and $R^6$ are not simultaneously methyl;
vii) if $R^2$-$R^6$=hydrogen,
  $R^1$ is not 2-pyridyl, 3-pyridyl, 4-pyridyl, 2-thienyl, 2-furanyl, 1-naphthyl, 2-naphthyl, phenyl, 4-chlorophenyl, 4-bromophenyl, 4-nitrophenyl, 4-hydroxyphenyl, 4-methoxyphenyl, 4-methylphenyl, p-biphenyl, 2-hydroxy-4-chlorophenyl, 3-nitrophenyl, 3-trifluoromethylphenyl, 2-hydroxyphenyl, 2-methoxyphenyl, 2-hydroxy-5-nitrophenyl, 2-hydroxy-5-methylphenyl;
viii) 6H-indeno-[1,2-b][1.8]naphthyridine, 5,6-dihydronaphtho[1,2-b][1.8]naphthyridine, 6H-[1]benzo-pyrano[4,3-b][1.8]naphthyridine or 6,7-dihydro-5H-benzo[6.7]cyclohepta[1,2-b][1.8]naphthyridine.

The invention further relates to herbicidal compositions and compositions for the control of harmful fungi, containing naphthyridines of the formula I, and methods for controlling undesired plant growth or for controlling harmful fungi using the naphthyridines of the formula I, including the individual compounds excluded by way of disclaimer of the substance.

Naphthyridines having very different substitution patterns have been known in chemistry for a long time and have found most varied applications. A majority of the compounds described comprise an amino or hydroxyl function or derivatives thereof in various positions of the ring. The biological action of such compounds extends from various pharmacological applications (e.g. EP-A 346 208, EP-A 391 185, J. Med. Chem. 1977, 20 838) through fungicidal applications (EP-A 410 762) to herbicidal applications (e.g. EP 329 012, WO 92/07468). An integral part of all these compounds are groups bonded to the naphthyridine via heteroatoms (nitrogen, oxygen or sulfur).

Data are fairly exceptionally disclosed on the biological activity of compounds of the formula I where $R^1$ is, for example, an unsubstituted or substituted phenyl ring and the radicals $R^2$–$R^6$ do not have the abovementioned meanings (OH, $NH_2$, $NR_2$).

Only Reddy et al. (Ind. J. Chem. 1988, 27B, 200–202; J. Indian Chem. 1986, 443–446) report on a weak antibacterial activity of compounds of the type I where $R^1$=substituted phenyl. Individual naphthyridines of the type I are further known from:

E. M. Hawes, D. G. Wibberley, J. Chem. Soc.(C) 1967, 1564 and loc. cit. 1966, pp. 315–320; T. Higashino et al., Chem. Pharm. Bull 1978, 26, 3242; Yakugaku Zasshi 1979, 99, 451–7 (CA 92(19): 163866a); D. K. Garecki, E. M. Hawes, J. Med. Chem. 1977, 20(1), 124 und loc. cit. 20(6), pages 838–840; J. P. Sauvage et al., Tetrahedron Lett. 1982, 23, 5291; R. P. Thummel et al., J. Heterocycl. Chem. 1986, 23, 689; E. J. S. Reddy et al., Natl. Acad. Sci. Lett. (India) 1985, 8, 19 (CA 103: 51079k).

The invention was based on the object of finding naphthyridines which have a good herbicidal action. Accordingly, it was found that compounds of the type I have strong herbicidal action against broad-leaved weeds and grasses pre-emergence and post-emergence. It was further found that compounds I do not damage, or only insignificantly damage important crop plants and thus are suitable for selectively controlling weeds in these crops. These crops include, for example, soybeans, cotton, wheat, rice and corn.

The compounds I according to the invention can be prepared by a multiplicity of methods (see e.g. Katritzky, Comprehensive Heterocyl. Chem. Vol 2, p. 607 ff).

The preparation of the compounds by the following processes proved particularly suitable for preparing I:

a) Condensation of aromatic and heteroaromatic ketones with 2-aminonicotinaldehydes (Friedländer synthesis, e.g. Hawes and Wibberley, J. Chem. Soc. 1966, 315; Caluwe, Tetrahedron 1980, 36, 2359–2407).

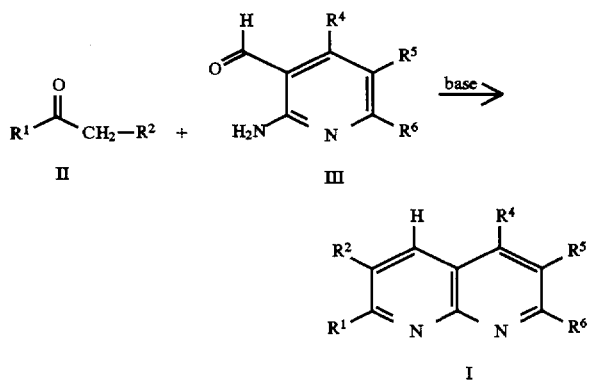

b) In a similar manner to this, appropriate aminoketones can also be employed.

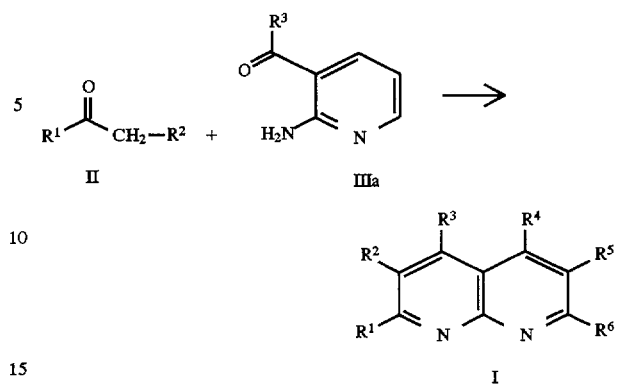

The reaction of active methylene ketones with 2-aminonicotinaldehydes or -ketones is preferably carried out in a solvent or diluent, for example in water, in an alcohol such as methanol, ethanol, propanol, isopropanol or ethoxyethanol, in liquid ammonia, in an ether such as tetrahydrofuran or dioxane, in an aromatic hydrocarbon such as benzene, toluene, chlorobenzene or nitrobenzene, in a polar aprotic solvent such as acetonitrile, dimethylformamide, dimethyl sulfoxide or N-methylpyrrolidone or in mixtures of these.

The reactions are advantageously carried out in the presence of an organic or inorganic base, those suitable being e.g. the hydroxides, hydrides, alkoxides, amides, carbonates and hydrogen carbonates of the alkali metals and alkaline earth metals. Alkali metal hydroxides such as lithium hydroxide, sodium hydroxide and potassium hydroxide, alkaline earth metal hydroxides such as barium hydroxide and calcium hydroxide, alkali metal hydrides such as sodium hydride and potassium hydride, alkaline earth metal hydrides such as calcium hydride, alkali metal alkoxides such as sodium methoxide, sodium ethoxide and potassium tert-butoxide, alkali metal amides such as sodium amide and lithium diisopropylamide, alkali metal carbonates and hydrogen carbonates such as sodium carbonate, sodium hydrogen carbonate, potassium bicarbonate and potassium hydrogen carbonate are particularly suitable. Among the organic bases, aliphatic amines such as triethylamine, dimethylamine, diethylamine and diisopropylamine, cycloaliphatic amines such as piperidine, morpholine, pyrrolidine, DBU and DABCO, and aromatic amines such as pyridine, N,N-dimethylaminopyridine and quinoline are particularly preferred.

If an amine is used as a base, the reaction can also be carried out solvent-free in an excess of the base.

Expediently, the starting materials II and III are employed in an approximately stoichiometric ratio or the reaction is carried out using an excess of methylene compound II of up to about 100 mol %, based on III.

The amount of base is not critical. As a rule, it is 10–50 mol %, but can also be employed in an excess.

When using an organic base, the reaction can be carried out without solvent in an excess of base, up to about 10 times the molar amount, based on the aminopyridine III.

In general, the reaction temperature is from 0° to 200° C., preferably from 20° to 150° C., in particular approximately 20°–30° C. (room temperature) or the boiling point of the respective solvent.

It is furthermore possible to carry out the reaction in the presence of an organic or inorganic acid. Those suitable for this are formic acid, acetic acid, propionic acid, pivalic acid, hydrochloric acid, hydrobromic acid, sulfuric acid, phosphoric acid, nitric acid or mixtures of these, for example acetic acid and sulfuric acid. If appropriate, the acids can be diluted with water. It may furthermore be advantageous to employ the acid as solvent.

c) As a substitute for the sensitive aminoaldehydes, pyrido [2,3-d]pyrimidines, for example, can be employed (Higashino et al., Chem. Pharm. Bull 1978, 28, 3242–3244).

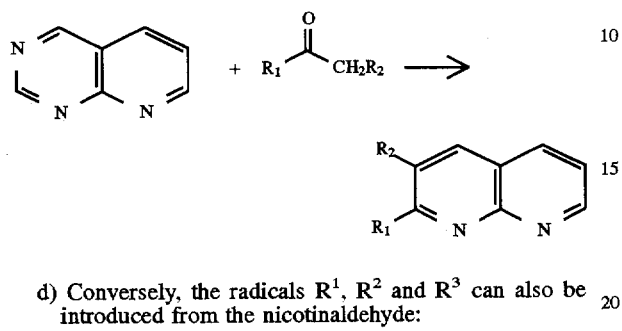

d) Conversely, the radicals $R^1$, $R^2$ and $R^3$ can also be introduced from the nicotinaldehyde:

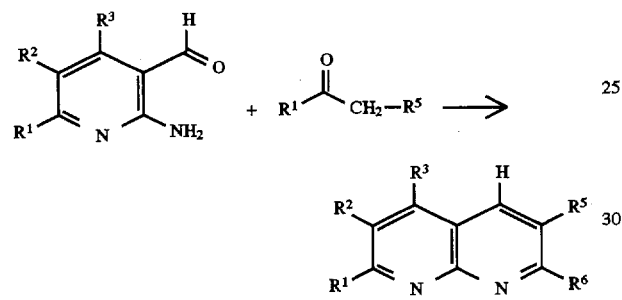

e) In some cases, the base-catalyzed condensation leads to an intermediate aminoketone:

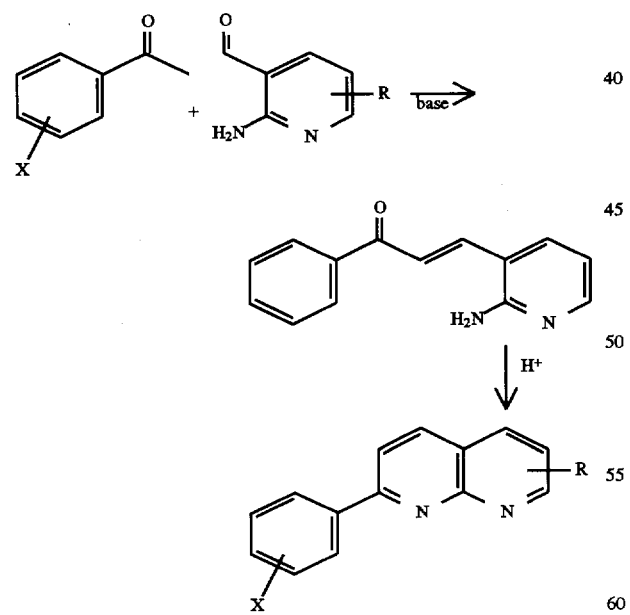

which does not react further and can be isolated. The compounds can then be cyclized in the presence of acid (e.g. $CH_3COOH/H_2SO_4$) to the desired naphthyridine.

f) Starting from substituted aminopyridines, the naphthyridines can be obtained by way of the Skraup synthesis by reaction of α,β-unsaturated aldehydes and ketones:

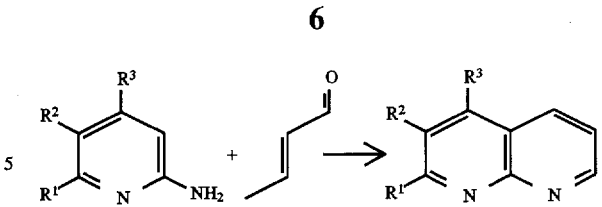

The synthesis of the aminonicotinaldehydes required for the Friedländer synthesis is carried out by generally known processes:

a) from 2-halo-3-cyanopyridines

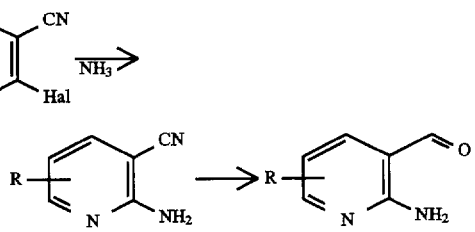

b) from pyrido[2,3-d]pyrimidines (Evans and Caluwe J. Org. Chem. 1975, 40, 1438–1439; Caluwe, J. Org. Chem. 1974, 39, 720–21).

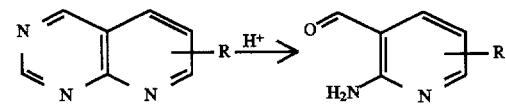

c) from 2-amino-3-methylpyridines (Hagen et al. DE-A 36 14 698)

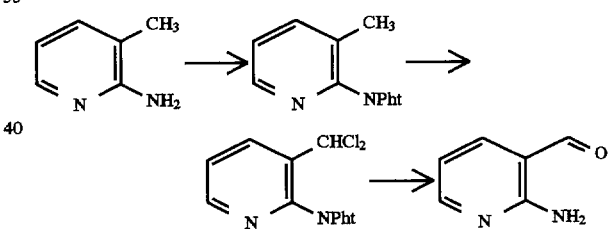

Pht = phthaloyl d) reaction of 1,3-butadiene-1,1-dicarbonitriles with $NH_3$ and subsequent reduction:

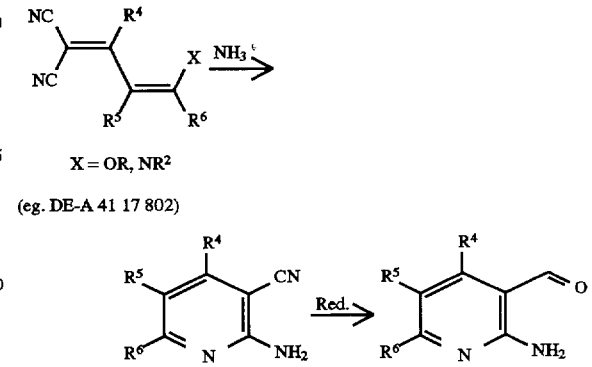

X = OR, $NR^2$ (eg. DE-A 41 17 802)

The ketones employed are usually commercially available, known from the literature or can be prepared in a generally known manner.

In formula I, the radicals mentioned may in some cases be substituted. If not individually put in concrete terms below, the expression unsubstituted or substituted means a $C_1$–$C_4$-alkyl group, $C_1$–$C_4$-alkoxy, $C_1$–$C_4$-haloalkyl, $C_1$–$C_4$-haloalkoxy or halogen, such as, in particular, fluorine, chlorine or bromine. The expression halogen stands for fluorine, chlorine, bromine or iodine, in particular fluorine and chlorine. Five- or six-membered saturated heterocycles are e.g. piperidyl, pyrolidinyl, tetrahydrofuranyl, tetrahydropyranyl, piperazinyl or morpholino. Aryl on its own or in combination means phenyl or naphthyl, heteroaryl, thienyl, furanyl, pyrrolyl, thiazolyl, oxazolyl, pyridyl, imidazolyl, 1,2,4-triazolyl or isoxazolyl.

Naphthyridines of the formula I are particularly preferred with respect to biological action if $R^1$ has the following meanings:

phenyl which is unsubstituted or is substituted by from one to four, in particular one or two substituents, selected from the group consisting of $C_1$–$C_8$-alkyl, in particular $C_1$–$C_4$-alkyl, such as methyl or ethyl, unsubstituted or substituted by halogen, $C_1$–$C_4$-alkoxy, amino, $C_1$–$C_4$-alkylamino, $C_1$–$C_4$-dialkylamino, $C_1$–$C_4$-thioalkyl, phenyl, phenoxy, thiophenyl, aminophenyl, $C_1$–$C_4$-alkylaminophenyl, it being possible for the five last-mentioned substituents in the phenyl ring to carry one to three substituents, selected from $C_1$–$C_4$-alkoxy, halogen, $C_1$–$C_4$-alkyl or nitro;

$C_2$–$C_8$-alkenyl or -alkynyl, in each case preferably having up to four C atoms and unsubstituted or substituted by halogen, $C_1$–$C_4$-alkoxy, $C_1$–$C_4$-thioalkyl, phenyl, phenoxy, thiophenyl, it being possible for the three last-mentioned substituents in the phenyl ring to carry one to three substituents selected from $C_1$–$C_4$-alkoxy, halogen, $C_1$–$C_4$-alkyl or nitro;

$C_3$–$C_8$-cycloalkyl, unsubstituted or substituted by halogen, $C_1$–$C_4$-alkoxy, amino, $C_1$–$C_4$-alkylamino, $C_1$–$C_4$-dialkylamino, $C_1$–$C_4$-thioalkyl, phenyl, phenoxy, thiophenyl, aminophenyl, $C_1$–$C_4$-alkylaminophenyl, it being possible for the five last-mentioned substituents in the phenyl ring to carry one to three substituents, selected from $C_1$–$C_4$-alkoxy, halogen, $C_1$–$C_4$-alkyl or nitro;

phenyl unsubstituted or substituted by up to three substituents selected from $C_1$–$C_4$-alkoxy, halogen, $C_1$–$C_4$-alkyl or nitro;

$C_1$–$C_5$-alkoxy, unsubstituted or substituted by halogen, $C_1$–$C_4$-alkoxy, cyano, $C_1$–$C_4$-dialkylamino, $C_1$–$C_4$-thioalkyl, phenyl, phenoxy, thiophenyl, aminophenyl, $C_1$–$C_4$-alkylaminophenyl, it being possible for the five last-mentioned substituents in the phenyl ring to carry one to three substituents, selected from $C_1$–$C_4$-alkoxy, halogen $C_1$–$C_4$-alkyl or nitro;

$C_1$–$C_5$-thioalkyl, unsubstituted or halogen-substituted, e.g. $C_1$–$C_4$-halothioalkyl such as chlorothiomethyl or dichlorothiomethyl;

a five or six-membered saturated heterocycle having one or two heteroatoms N, O or S such as e.g. thienyl, furanyl, pyrrolyl, thiazolyl, oxazolyl, isooxazolyl, imidazolyl, 1,2,4-triazolyl, isothiazolyl, 1,2,4-oxadiazolyl or 1,3,4-thiadiazolyl;

or a five- or six-membered heteroaromatic having one to three nitrogen atoms or one nitrogen atom and a further O or S atom or having only one heteroatom oxygen or sulfur, such as, for example, pyridyl, pyrimidyl, pyrazinyl, triazinyl; the heterocyclic or heteroaromatic radicals mentioned, which are bonded via a C atom or an N atom, in each case being unsubstituted or substituted one to three times, in particular once, by $C_1$–$C_4$-alkoxy, halogen, $C_1$–$C_4$-alkyl, cyano, hydroxyl, amino, $C_1$–$C_4$-alkylamino, $C_1$–$C_4$-dialkylamino, $C_1$–$C_4$-alkoxycarbonyl or nitro;

in addition the phenyl radical $R^1$ can be substituted by: hydroxyl, an $OC(O)R^{14}$ group, amino, an $NR^{15}R^{16}$ group, halogen such as fluorine, chlorine or bromine, cyano, nitro, carboxyl, an $R^7SO_2$ group, $C(O)R^8$, $C(Y)R^9$ where Y=O or $NR^{13}$, a $C(VR^{10}WR^{11})R^{12}$ group where V and W independently of one another are oxygen or sulfur, and $R^7$–$R^{16}$ are:

$R^7$ is $C_1$–$C_8$-alkyl, $C_1$–$C_8$-haloalkyl, phenyl, $C_1$–$C_8$-monoalkyl- or $C_1$–$C_8$-dialkylamino, $C_5$–$C_8$-cycloalkylamino;

$R^8$ is hydroxyl, amino, $C_1$–$C_8$-monoalkyl- or $C_1$–$C_8$-dialkylamino, $C_5$–$C_8$-cycloalkylamino, $C_3$–$C_8$-alkoxy;

$R^9$ is hydrogen, $C_1$–$C_8$-alkyl, $C_3$–$C_8$-cycloalkyl, $C_1$–$C_8$-haloalkyl, phenyl, heteroaryl;

$R^{10}$ and $R^{11}$ are $C_1$–$C_8$-alkyl, $C_1$–$C_6$-haloalkyl, $C_1$–$C_4$-alkoxy($C_1$–$C_6$)-alkyl, or $R^{10}$ and $R^{11}$ together form a di-, tri- or tetramethylene chain which is unsubstituted or substituted by one or two $C_1$–$C_8$-alkyl, $C_1$–$C_6$-haloalkyl, $C_1$–$C_4$-alkoxy($C_1$–$C_6$)-alkyl groups or an oxo group;

$R^{12}$ is hydrogen, $C_1$–$C_6$-alkyl, $C_3$–$C_8$-cycloalkyl, $C_1$–$C_8$-haloalkyl, phenyl, heteroaryl;

$R^{13}$ is $C_1$–$C_8$-alkyl, $C_3$–$C_8$-cycloalkyl, $C_1$–$C_4$-alkoxy($C_1$–$C_6$)-alkyl, $C_1$–$C_8$-aminoalkyl, phenyl, aryl($C_1$–$C_6$)-alkyl, heteroaryl, hydroxyl, unsubstituted or substituted $C_6$–$C_{10}$-aryloxy, unsubstituted or substituted $C_1$–$C_8$-alkoxy, amino, $C_1$–$C_8$-monoalkyl- or $C_1$–$C_8$-dialkylamino, $C_5C_8$-cycloalkylamino, unsubstituted or substituted $C_6C_{10}$-arylamino;

$R^{14}$ is $C_1$–$C_5$-alkyl, unsubstituted or substituted phenyl, $C_1$–$C_5$-alkoxy, $C_1$–$C_5$-haloalkoxy, benzyloxy, amino, alkylamino, dialkylamino, a saturated five or six-membered heterocycle bonded via N;

$R^{15}$ is hydrogen, $C_1$–$C_5$-alkyl, unsubstituted or substituted phenyl;

$R^{16}$ is hydrogen, $C_1$–$C_5$-alkyl, unsubstituted or substituted phenyl, a —$C(O)R^{14}$ group, or $R^{16}$ together with $R^{15}$ forms a four- or five-membered methylene chain which, in turn, can be substituted by one or two methyl groups and in which one methylene group can be replaced by oxygen;

$R^1$ is additionally preferably a phenyl radical in which two directly adjacent positions are bonded to one another via a tri- or tetramethylene group which, in turn, can carry one to three $C_1$–$C_3$-alkyl, $C_1$–$C_2$-alkoxy and/or halogen substituents, and the other positions are unsubstituted or are substituted on the phenyl ring by one of the abovementioned substituents, in particular by $C_1$–$C_4$-alkyl, e.g. methyl, ethyl, i-propyl, n-propyl, n-butyl, i-butyl;

$R^1$ is furthermore phenyl which is bonded to $R^2$ via the ortho position to give a chain of from one to four methylene groups or from one to three methylene groups and an oxygen atom, it being possible for each methylene group to carry one or two $C_1$–$C_3$-alkyl radicals, e.g. to give a —$CH_2$—$CH_2$—$CH_2$—, —$CH_2$—$CH_2$—$CH_2$—$CH_2$-, —$CH_2$—O—$CH_2$—$CH_2$—, —$CH_2$ ($CH_3$)—$CH_2$—$CH_2$—$CH_2$—, —$CH_2$—O—$CH_2$—, —$C(CH_3)_2$—$CH_2$—$CH_2$—, —$CH(CH_3)$—$CH_2$—$CH_2$— chain.

$R^1$ is furthermore a heteroaromatic, selected from the group consisting of 2-thienyl, 2-benzothienyl, 3-thienyl, 2-furanyl, 3-furanyl, 2-benzofuranyl, 2-pyrrolyl, 3-pyrrolyl, 2-thiazolyl, 4-thiazolyl, 5-thiazolyl, 2-oxazolyl, 4-oxazolyl, 5-oxazolyl, 2-pyridyl, 3-pyridyl, 4-pyridyl, 2-pyrimidinyl, 4-pyrimidinyl, 5-pyrimidinyl, 2-benzothiazolyl, 2-benzoxazolyl, particularly preferably 2- or 3-thienyl, it being possible for the heteroaromatics to carry one or two of the following substituents:

$C_1$–$C_8$-alkyl, $C_3$–$C_8$-cycloalkyl, $C_1$–$C_8$-haloalkyl, phenyl, $C_1$–$C_5$-alkoxy, $C_1$–$C_3$-haloalkoxy, halogen, cyano, nitro, carboxyl, sulfonylmethyl, $C_1$–$C_4$-alkoxycarbonyl, carbamoyl, $C_1$–$C_4$-alkylcarbamoyl, di-($C_1$–$C_4$)-alkylcarbamoyl.

The radicals $R^2$–$R^6$ in formula I are, for example, hydrogen, $C_1$–$C_8$-alkyl, in particular $C_1$–$C_4$-alkyl such as methyl, ethyl or propyl, $C_2$–$C_8$-alkenyl, in particular $C_2$–$C_4$-alkenyl such as vinyl or allyl, $C_3$–$C_8$-cycloalkyl, in particular cyclopentyl, cyclohexyl or cyclopropyl, $C_1$–$C_8$-haloalkyl, e.g. $C_1$–$C_4$-haloalkyl such as trifluoromethyl, trichloromethyl, fluoroethyl or chloroethyl, $C_1$–$C_4$-alkoxy ($C_1$–$C_6$)-alkyl such as methoxymethyl, methoxyethyl, ethoxymethyl or ethoxyethyl, $C_1$–$C_8$-, in particular $C_1$–$C_4$-aminoalkyl such as aminomethyl or aminoethyl, phenyl or benzyl, in each case unsubstituted or substituted, in particular by one to three radicals such as $C_1$–$C_4$-alkyl, halogen, $C_1$–$C_4$-haloalkyl, $C_1$–$C_4$-alkoxy or nitro; heteroaryl linked via a C atom, e.g. pyridyl, thienyl or furanyl, it being possible for the heteroaromatic to be substituted, e.g. by methyl, chlorine, nitro or cyano;

$R^2$–$R^6$ are furthermore cyano, nitro, carboxyl, sulfonylmethyl, $C_1$–$C_4$-alkoxycarbonyl, carbamoyl, $C_1$–$C_4$-alkylcarbamoyl, di($C_1$–$C_4$)-alkylcarbamoyl, $C_1$–$C_4$-alkanoyl such as acetyl, benzoyl.

Two adjacent radicals $R^4$ and $R^5$ or $R^5$ and $R^6$ can furthermore together form a —$CH_2$—($CH_2$)$_n$—$CH_2$ chain where n=1 to 3 or a fused aromatic ring, i.e. can together form a —CH=CH—CH=CH— bridge.

The compounds according to the invention have a particularly strong herbicidal action if:

$R^1$ has the meaning phenyl and at least one substituent is in the ortho position of the phenyl ring;

$R^1$ has the meaning unsubstituted phenyl and the substituent $R^2$ does not have the meaning hydrogen.

If the substituent $R^1$ has the meaning substituted phenyl, the following meanings are to be regarded as particularly preferred:

phenyl substituted by:

2-methyl, 3-methyl, 4-methyl, 2-ethyl, 3-ethyl, 4-ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 3-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 4-phenyl, 2-sulfonylmethyl, 3-sulfonylmethyl, 4-sulfonylmethyl, 3-t-butoxy, 4-t-butoxy, 3-O-CH(CH$_3$) CO$_2$Me, 4-O-CH(CH$_3$)CO$_2$Me, 3-N-piperidyl, 4-N-piperidyl, 4-N-pyrrolidinyl, 3-N-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4, 5-trifluoro, 2,4,6-trifluoro, 2,3-dichloro, 2,4-dichloro, 2,5-dichloro, 2,6-dichloro, 2,3,4-trichloro, 2,3,5-trichloro, 2,3, 6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6-ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-methoxy, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl, 2-chloro-3-methyl, 2-chloro-3-fluoro, 2-chloro-3-methoxy, 2-chloro-3-nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2-methyl-6-nitro, 2-methyl-5-trifluoromethoxy, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl, 2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

If the substituent $R^1$ has the meaning substituted 2-thienyl, the following meanings are to be regarded as particularly preferred:

2-thienyl substituted by:

5-methyl, 4-methyl, 3-methyl, 3,5-dimethyl, 5-ethyl, 3-ethyl, 5-t-butyl, 5-t-butyl-4-amino, 5-phenyl, 5-phenyl-4-amino, 5-(2-thienyl), 5-chloro, 5-bromo, 5-cyano, 5-nitro.

If the substituent $R^1$ has the meaning substituted 3-thienyl, the following meanings are to be regarded as particularly preferred:

3-thienyl substituted by:

5-methyl, 2,5-methyl, 5-ethyl, 2-methyl, 2-ethyl, 5-chloro, 5-bromo, 2,5-dichloro, 2,5-dibromo, 5-nitro, 5-phenyl.

The following meanings are particularly preferred for the substituent R²:

R²=hydrogen, methyl, ethyl, n-propyl, isopropyl, n-butyl, s-butyl, t-butyl, trifluoromethyl, cyclopropyl, cyclopentyl, cyclohexyl, phenyl, benzyl, cyano, carbomethoxy, carboethoxy, sulfonylmethyl, sulfonylphenyl.

The following are particularly preferred for the substituents R³-R⁶:

R³-R⁶=hydrogen, phenyl, thienyl, methyl, ethyl, i-propyl, n-propyl, trifluoromethyl, benzyl, nitro, cyano.

The compounds mentioned in the following are particularly preferred:

Compounds of the formula Ia

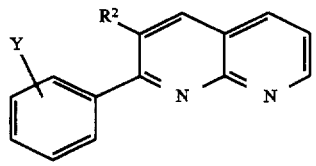

where the substituents have the following meanings:

R²=hydrogen and Y is in each case:

2-methyl, 3-methyl, 4-methyl, 2-ethyl, 3-ethyl, 4-ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 3-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 4-phenyl, 2-sulfonylmethyl, 3-sulfonylmethyl, 4-sulfonylmethyl, 3-t-butoxy, 4-t-butoxy, 3—O—CH(CH₃)CO₂Me, 4—O—CH(CH₃)CO₂Me, 3-N-piperidyl, 4-N-piperidyl, 4-N-pyrrolidinyl, 3-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4,5-trifluoro, 2,4,6-trifluoro, 2,3-dichloro, 2,4-dichloro, 2,5-dichloro, 2,6-dichloro, 2,3,4-trichloro, 2,3,5-trichloro, 2,3,6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6 ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl, 2-chloro-3-methyl, 2-chloro-3-fluoro, 2-chloro-3-methoxy, 2-chloro-3-nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2-methyl-6-nitro, 2-methyl-5-trifluoromethyl, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl, 2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

Compounds of the formula Ia where R²=methyl and Y is in each case:

2-methyl, 3-methyl, 4-methyl, 2-ethyl, 3-ethyl, 4. ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 3-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 4-phenyl, 2-sulfonylmethyl, 3-sulfonylmethyl, 4-sulfonylmethyl, 3-t-butoxy, 4-t-butoxy, 3—O—CH(CH₃)CO₂Me, 4—O—CH(CH₃)CO₂Me, 3-N-piperidyl, 4-N-piperidyl, 4-N-pyrrolidinyl, 3-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4,5-trifluoro, 2,4,6-trifluoro, 2,3-dichloro, 2,4-dichloro, 2,5-dichloro, 2,6-dichloro, 2,3,4-trichloro, 2,3,5-trichloro, 2,3,6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6-ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-methoxy, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl, 2-chloro-3-methyl, 2-chloro-3-fluoro, 2-chloro-3-methoxy, 2-chloro-3-nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2-methyl-6-nitro, 2-methyl-5-trifluoromethoxy, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl, 2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

Compounds of the formula Ia where $R^2$=ethyl and Y is in each case:

2-methyl, 3-methyl, 4-methyl, 2-ethyl, 3-ethyl, 4-ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 3-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 4-phenyl, 2-sulfonylmethyl, 3-sulfonylmethyl, 4-sulfonylmethyl, 3-t-butoxy, 4-t-butoxy, 3—O—CH(CH$_3$)CO$_2$Me, 4—O—CH(CH$_3$)CO$_2$Me, 3-N-piperidyl, 4-N-piperidyl, 4-N-pyrrolidinyl, 3-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4,5-trifluoro, 2,4,6-trifluoro, 2,3-dichloro, 2,4-dichloro, 2,5-dichloro, 2,6-dichloro, 2,3,4-trichloro, 2,3,5-trichloro, 2,3,6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6-ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-methoxy, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl, 2-chloro-3-methyl, 2-chloro-3-fluoro, 2-chloro-3-methoxy, 2-chloro-3-nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2-methyl-6-nitro, 2-methyl-5-trifluoromethoxy, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl, 2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

Compounds of the formula Ia where $R^2$=isopropyl and Y is in each case:

2-methyl, 3-methyl, 4-methyl, 2-ethyl, 3-ethyl, 4-ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 3-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 4-phenyl, 2-sulfonylmethyl, 3-sulfonylmethyl, 4-sulfonylmethyl, 3-t-butoxy, 4-t-butoxy, 3-O—CH(CH$_3$)CO$_2$Me, 4-O—CH(CH$_3$)CO$_2$Me, 3-N-piperidyl, 4-N-piperidyl, 4-N-pyrrolidinyl, 3-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4,5-trifluoro, 2,4,6-trifluoro, 2,3-dichloro, 2,4-dichloro, 2,5-dichloro, 2,6-dichloro, 2,3,4-trichloro, 2,3,5-trichloro, 2,3,6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6-ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-methoxy, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl/2-chloro-3-methyl, 2-chloro-3-fluoro, 2-chloro-3-methoxy, 2-chloro-3-nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2methyl-6-nitro, 2-methyl-5-trifluoromethoxy, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl, 2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

Compounds of the formula Ia where $R^2$=ethyl and Y is in each case:

2-methyl, 3-methyl, 4-methyl, 2-ethyl, 3-ethyl, 4-ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 3-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 4-phenyl, 2-sulfonylmethyl, 3-sulfonylmethyl, 4-sulfonylmethyl, 3-t-butoxy, 4-t-butoxy, 3—O—CH(CH$_3$)CO$_2$Me, 4—O—CH(CH$_2$)CO$_2$Me, 3-N-piperidyl, 4-N-piperidyl, 4-N-pyrrolidinyl, 3-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4,5-trifluoro, 2,4,6-trifluoro, 2,3-dichloro, 2,4-dichloro, 2,5-dichloro, 2,6-dichloro, 2,3,4-trichloro, 2,3,5-trichloro, 2,3,6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6-ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-methoxy, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl, 2-chloro-3-methyl, 2-chloro-3-fluoro, 2-chloro-3-methoxy, 2-chloro-3- nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2-methyl-6-nitro, 2-methyl-5-trifluoromethoxy, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl,2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

Compounds of the formula Ia where $R^2$=trifluoromethyl and Y is in each case:

2-methyl, 3-methyl, 4-methyl, 2-ethyl, 3-ethyl, 4-ethyl, 2-propyl, 3-propyl, 4-propyl, 2-i-propyl, 3-i-propyl, 4-i-propyl, 2-n-butyl, 3-n-butyl, 4-n-butyl, 2-s-butyl, 3-s-butyl, 4-s-butyl, 2-t-butyl, 3-t-butyl, 4-t-butyl, 2-benzyl, 3-benzyl, 4-benzyl, 2-cyclopropyl, 3-cyclopropyl, 4-cyclopropyl, 2-trifluoromethyl, 3-trifluoromethyl, 4-trifluoromethyl, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-thiomethyl, 3-thiomethyl, 4-thiomethyl, 2-fluoro, 3-fluoro, 4-fluoro, 2-chloro, 3-chloro, 4-chloro, 2-bromo, 3-bromo, 4-bromo, 2-nitro, 3-nitro, 4-nitro, 2-cyano, 3-cyano, 4-cyano, 2-carbomethoxy, 3-carbomethoxy, 4-carbomethoxy, 2-carboethoxy, 3-carboethoxy, 4-carboethoxy, 2-carbamoyl, 3-carbamoyl, 4-carbamoyl, 2-N-methylcarbamoyl, 3-N-methylcarbamoyl, 4-N-methylcarbamoyl, 2-N,N-dimethylcarbamoyl, 3-N,N-dimethylcarbamoyl, 4-N,N-dimethylcarbamoyl, 2-N,N-diethylcarbamoyl, 3-N,N-diethylcarbamoyl, 4-N,N-diethylcarbamoyl, 2-amino, 3-amino, 4-amino, 2-N-methylamino, 2-N-methylamino, 4-N-methylamino, 2-dimethylamino, 3-dimethylamino, 4-dimethylamino, 2-N-acetylamino, 3-N-acetylamino, 4-N-acetylamino, 2-hydroxy, 3-hydroxy, 4-hydroxy, 2-phenyl, 3-phenyl, 3-phenyl, 2-sulfonylmethyl, 3-sulfonylmethyl, 4-sulfonylmethyl, 3-t-butoxy, 4-t-butoxy, 3-O—CH(CH$_3$)CO$_2$Me, 4-O—CH(CH$_3$)CO$_2$Me, 3-N-piperidyl, 4-N-piperidyl, 4-N-pyrrolidinyl, 3-pyrrolidinyl, 3-N-pyrrolyl, 4-N-pyrrolyl, 2,3-difluoro, 2,4-difluoro, 2,5-difluoro, 2,6-difluoro, 2,3,4-trifluoro, 2,3,5-trifluoro, 2,3,6-trifluoro, 2,4,5-trifluoro, 2,4,6-trifluoro, 2,3-dichloro, 2,4-dichloro, 2,5-dichloro, 2,6-dichloro, 2,3,4-trichloro, 2,3,5-trichloro, 2,3,6-trichloro, 2,4,5-trichloro, 2,4,6-trichloro, 2,3-dimethyl, 2,4-dimethyl, 2,5-dimethyl, 2,6-dimethyl, 2,3,4-trimethyl, 2,3,5-trimethyl, 2,3,6-trimethyl, 2,4,5-trimethyl, 2,4,6-trimethyl, 2-fluoro-6-methyl, 2-fluoro-6-ethyl, 2-fluoro-6-chloro, 2-fluoro-6-methoxy, 2-fluoro-6-N,N-dimethylamino, 2-fluoro-6-trifluoromethyl, 2-fluoro-6-carbomethoxy, 2-fluoro-6-nitro, 2-fluoro-5-methyl, 2-fluoro-5-chloro, 2-fluoro-5-methoxy, 2-fluoro-5-N,N-dimethylamino, 2-fluoro-5-trifluoromethyl, 2-fluoro-5-carbomethoxy, 2-fluoro-5-nitro, 2-fluoro-5-trifluoromethoxy, 2-fluoro-4-methyl, 2-fluoro-4-chloro, 2-fluoro-4-methoxy, 2-fluoro-4-N,N-dimethylamino, 2-fluoro-4-trifluoromethyl, 2-fluoro-4-carbomethoxy, 2-fluoro-4-nitro, 2-fluoro-4-cyano, 2-fluoro-4-sulfonylmethyl, 2-fluoro-3-methyl, 2-fluoro-3-chloro, 2-fluoro-3-methoxy, 2-fluoro-3-N,N-dimethylamino, 2-fluoro-3-trifluoromethyl, 2-fluoro-3-carbomethoxy, 2-fluoro-3-nitro, 2-fluoro-3-trifluoromethoxy, 2-fluoro-4-chloro-5-methoxy, 2-chloro-6-methyl, 2-chloro-6-ethyl, 2-chloro-6-fluoro, 2-chloro-6-methoxy, 2-chloro-6-nitro, 2-chloro-6-dimethylamino, 2-chloro-6-trifluoromethoxy, 2-chloro-6-carbomethoxy, 2-chloro-5-methyl, 2,4-dichloro-5-methyl, 2-chloro-5-fluoro, 2,4-dichloro-5-fluoro, 2-chloro-5-methoxy, 2-chloro-5-nitro, 2-chloro-5-dimethylamino, 2-chloro-5-trifluoromethoxy, 2-chloro-5-carbomethoxy, 2-chloro-5-trifluoromethoxy, 2-chloro-4-methyl, 2-chloro-4-fluoro, 2-chloro-4,5-difluoro, 2-chloro-4-methoxy, 2-chloro-4-nitro, 2-chloro-4-dimethylamino, 2-chloro-4-trifluoromethoxy, 2-chloro-4-carbomethoxy, 2-chloro-4-cyano, 2-chloro-4-sulfonylmethyl, 2-chloro-3-methyl, 2-chloro-3-fluoro, 2-chloro-3-methoxy, 2-chloro-3-nitro, 2-chloro-3-dimethylamino, 2-chloro-3-trifluoromethoxy, 2-chloro-3-carbomethoxy, 2-chloro-3-trifluoromethoxy, 2-methyl-6-fluoro, 2-methyl-6-chloro, 2-methyl-6-ethyl, 2-methyl-6-methoxy, 2-methyl-6-dimethylamino, 2-methyl-6-trifluoromethyl, 2-methyl-6-carbomethoxy, 2-methyl-6-nitro, 2-methyl-5-fluoro, 2-methyl-5-chloro, 2-methyl-5-methoxy, 2-methyl-5-dimethylamino, 2-methyl-5-trifluoromethyl, 2-methyl-5-carbomethoxy, 2-methyl-6-nitro, 2-methyl-5-trifluoromethoxy, 2-methyl-4-fluoro, 2-methyl-4-chloro, 2-methyl-4-methoxy, 2-methyl-4-dimethylamino, 2-methyl-4-trifluoromethyl, 2-methyl-4-carbomethoxy, 2-methyl-4-nitro, 2-methyl-4-cyano, 2-methyl-4-sulfonylmethyl, 2-methyl-3-fluoro, 2-methyl-3-chloro, 2-methyl-3-methoxy, 2-methyl-3-dimethylamino, 2-methyl-3-trifluoromethyl, 2-methyl-3-carbomethoxy, 2-methyl-3-nitro, 2-methyl-3-trifluoromethoxy.

Compounds of the formula Ib are furthermore preferred

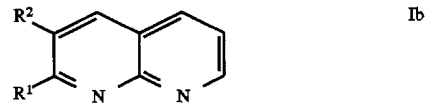

where the substituents have the following meanings:

$R^2$=n-propyl and $R^1$ is phenyl, 2-chlorophenyl, 2-fluorophenyl, 2,6-difluorophenyl, 2-methylphenyl, 2-ethylphenyl and 2-thienyl;

$R^2$=n-butyl and. $R^1$ is phenyl, 2-chlorophenyl, 2-fluorophenyl, 2,6-difluorophenyl, 2-methylphenyl, 2-ethylphenyl and 2-thienyl;

$R^2$=t-butyl and $R^1$ is phenyl, 2-chlorophenyl, 2-fluorophenyl, 2,6-difluorophenyl, 2-methylphenyl, 2-ethylphenyl and 2-thienyl;

$R^2$=s-butyl and $R^1$ is phenyl, 2-chlorophenyl, 2-fluorophenyl, 2,6-difluorophenyl, 2-methylphenyl, 2-ethylphenyl and 2-thienyl;

$R^2$=benzyl and $R^1$ is phenyl, 2-chlorophenyl, 2-fluorophenyl, 2,6-difluorophenyl, 2-methylphenyl, 2-ethylphenyl and 2-thienyl;

$R^2$=cyclopentyl and $R^1$ is phenyl, 2-chlorophenyl, 2-fluorophenyl, 2,6-difluorophenyl, 2-methylphenyl, 2-ethylphenyl and 2-thienyl;

$R^2$=cyclohexyl and $R^1$ is phenyl, 2-chlorophenyl, 2-fluorophenyl, 2,6-difluorophenyl, 2-methylphenyl, 2-ethylphenyl and 2-thienyl;

$R^2$=phenyl and $R^1$ is phenyl, 2-chlorophenyl, 2-fluorophenyl, 2,6-difluorophenyl, 2-methylphenyl, 2-ethylphenyl and 2-thienyl;

$R^2$=carboethoxy and $R^1$ is phenyl, 2-chlorophenyl, 2-fluorophenyl, 2,6-difluorophenyl, 2-methylphenyl, 2-ethylphenyl and 2-thienyl;

$R^2$=carbomethoxy and $R^1$ is phenyl, 2-chlorophenyl, 2-fluorophenyl, 2,6-difluorophenyl, 2-methylphenyl, 2-ethylphenyl and 2-thienyl;

$R^2$=cyano and $R^1$ is phenyl, 2-chlorophenyl, 2-fluorophenyl, 2,6-difluorophenyl, 2-methylphenyl, 2-ethylphenyl and 2-thienyl;

$R^2$=sulfonylmethyl and $R^1$ is phenyl, 2-chlorophenyl, 2-fluorophenyl, 2,6-difluorophenyl, 2-methylphenyl, 2-ethylphenyl and 2-thienyl;

$R^2$=sulfonylphenyl and $R^1$ is phenyl, 2-chlorophenyl, 2-fluorophenyl, 2,6-difluorophenyl, 2-methylphenyl, 2-ethylphenyl and 2-thienyl.

As herbicides, the compounds I or the herbicidal compositions containing them and their environmentally tolerable salts e.g. of alkali metals and alkaline earth metals can very effectively control broad-leaf weeds and grass weeds in crops such as wheat, rice, maize, soybeans and cotton without damaging the crop plants, an effect which occurs especially even at low application rates.

The compounds I or the herbicidal compositions containing them can be applied by spraying, atomizing, dusting, broadcasting or watering, for example in the form of directly sprayable aqueous solutions, powders, suspensions, even high-percentage aqueous, oily or other suspensions or dispersions, emulsions, oil dispersions, pastes, dusting compositions, broadcasting compositions or granules. The application forms depend on the intended uses; in each case they should if possible ensure the finest dispersion of the active compounds according to the invention.

The compounds I are generally suitable for preparing directly sprayable solutions, emulsions, pastes or oil dispersions. Suitable inert additives are mineral oil fractions of medium to high boiling point, such as kerosene or diesel oil, additionally coal tar oils and oils of vegetable or animal origin, aliphatic, cyclic and aromatic hydrocarbons, e.g. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can also be prepared, which are suitable for dilution with water.

Suitable surface-active substances are the alkali metal, alkaline earth metal and ammonium salts of aromatic sulfonic acids, e.g. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenol or tributylphenol polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, e.g. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (by NMR spectrum).

The compounds I according to the invention can furthermore be formulated, for example, as follows:

I. 20 parts by weight of the compound No. 1.11 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 1.12 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100.000 parts by weight of water, an aqueous dispersion is obtained which contains 0.02% by weight of the active compound.

III. 20 parts by weight of the active compound No. 1.16 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 1.11 are well mixed with 3 parts by weight of the sodium salt of diisobutylnaphthalene α-sulfonic acid, 17 parts by weight of the sodium salt of a lignosulfonic acid from a sulfite waste liquor and 60 parts by weight of powdered silica gel and the mixture is ground in a hammermill. By finely dispersing the mixture in 20,000 parts by weight of water, a spray mixture is obtained which contains 0.1% by weight of the active compound.

V. 3 parts by weight of the active compound No. 1.12 are mixed with 97 parts by weight of finely divided kaolin. In this way a dusting composition is obtained which contains 3% by weight of the active compound.

VI. 20 parts by weight of the active compound No. 1.16 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and. 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the target of control, time of year, target plants and stage of growth, the application rates of active compound are from 0.001 to 3.0, preferably from 0.01 to 1.0, kg/ha of active substance (a.s.).

In consideration of the variety of application methods, the compounds I according to the invention or compositions containing them can additionally be employed in a further number of crop plants for the elimination of undesired plants. Suitable crops are, for example, the following:

Alliumcepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N. rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.

To widen the spectrum of action and to achieve a synergistic effect, the naphthyridines I mixture can be mixed with numerous representatives of other herbicidal or growth-regulating active compound groups and applied jointly. For example, suitable components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry e.g. a carboxyl or carbimino group in the 2-position, quinolinecarboxylic acid derivatives, imidazolinones, sulfonamides, sulfonylureas, aryloxy- or heteroaryloxyphenoxypropionic acids and their salts, esters and amides and others.

Additionally, it may be useful to apply the compounds I on their own or together in combination with other herbicides, additionally mixed with further crop protection agents, for example with agents for controlling pests or phytopathogenic fungi and bacteria. Further of interest is the miscibility with mineral salt solutions, which are employed for the elimination of nutrition and trace element deficiencies. Non-phytotoxic oils and oil concentrates can also be added.

The naphthyridines I are moreover suitable as fungicides.

The compounds I are distinguished by an outstanding activity against a broad spectrum of phytopathogenic fungi, in particular from the class of Ascomycetes and Basidiomycetes. They are systemically active in some cases and can be employed as foliar and soil fungicides.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

They are specifically suitable for the control of the following plant diseases: Erysiphe graminis (powdery mildew) in cereals, Erysiphe cichoracearum and Sphaerotheca fuliginea on cucurbits, Podosphaera leucotricha on apples, Uncinula necator on vines, Puccinia species on cereals, Rhizoctonia species on cotton and lawns, Ustilago species on cereals and sugar cane, Venturia inaequalis (scab) on apples; Helminthosporium species on cereals, Septoria nodorumon wheat, Botrytis cinerea (gray mold) on strawberries, vines, Cercospora arachidicola on groundnuts, Pseudocercosporella herpotrichoides on wheat, barley, Pyricularia oryzae on rice, Phytophthora infestans on potatoes and tomatoes, Fusarium and Verticillium species on various plants, PLasmopara viticola on vines, Alternaria species on vegetables and fruit.

The compounds I are applied by treating the fungi or the plants, seeds, materials or the soil to be protected from fungal attack with a fungicidally effective amount of the active compounds. They are applied before or after the infection of the materials, plants or seeds by the fungi.

They can be converted into the customary formulations, such as solutions, emulsions, suspensions, dusts, powders, pastes and granules. The application form depends on the particular intended use; they should in any case guarantee a fine and uniform dispersion of the orthosubstituted benzyl ester of a cyclopropane-carboxylic acid. The formulations are prepared in a known manner, e.g. by extending the active compound with solvents and/or carriers, if desired using emulsifiers and dispersants, it also being possible to use other organic solvents as auxilliary solvents when water is used as a diluent. Suitable auxilliary substances for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly disperse silicic acid, silicates); emulsifiers such as nonionic and anionic emulsifiers (e.g. polyoxyethylene fatty alcohol ethers, alkyl-sulfonates and arylsulfonates) and dispersants such as lignin-sulfite waste liquors and methylcellulose.

The fungicidal compositions in general contain from 0.1 to 95, preferably from 0.5 to 90, % by weight of active compound.

Depending on the type of effect desired, the application rates are from 0.01 to 2.0 kg of active compound per ha.

In seed treatment, active compound amounts of from 0.001 to 0.1 g, preferably 0.01 to 0.05 g, per kilogram of seed are in general needed.

The compositions according to the invention can also be present as fungicides together with other active compounds in the application form, e.g. with herbicides, insecticides, growth regulators, fungicides or alternatively with fertilizers.

On mixing with fungicides, in many cases an increase in the fungicidal spectrum of action is obtained here.

EXAMPLES

Example 1

2-Phenyl-3-isopropyl-1,8-naphthyridine

2-Aminonicotinaldehyde (1.5 g, 12.3 mmol) and isobutyl phenyl ketone (2.09 g, 12.9 mmol) are dissolved in 12 ml of methanol and the mixture is treated dropwise at room temperature with 1.5 ml of 40% KOH and heated to reflux for 5 h. After aqueous workup, the crude product is purified by column chromatography on $SiO_2$ (cyclohexane/ethyl acetate 2:8). 600 mg (20% yield) of the desired compound are obtained. M.p. 165°–166° C.

Example 2

2-(2'-Fluorophenyl)-1,8-naphthyridine

2-Aminonicotinaldehyde (1.0 g, 8.2 mmol) and 2-fluoroacetophenone (1.19 g, 8.6 mmol) are dissolved in 8 ml of MeOH and the mixture is treated dropwise at room temperature with 40% aq. KOH. It is stirred overnight and then poured onto ice, and the product is filtered off with suction. 1.36 g (74% yield) of the desired product are obtained. M.p. 111°–114° C.

Example 3

2-(2',6'-Difluorophenyl)-1,8-naphthyridine

2-Aminonicotinaldehyde (2.44 g, 20 mmol) and 2,6-difluoroacetophenone (3.28 g, 21 mmol) are dissolved in 20 ml of MeOH. The mixture is treated dropwise with 3 ml of 40% KOH and, after the exothermic reaction has subsided, it is poured onto water and the residue which is deposited is filtered off with suction. 3.8 g (79% yield) of the desired product are obtained. M.p. 100°–103° C.

Example 4

2-(2'-Trifluoromethyl)-1,8-naphthyridine

2-Aminonicotinaldehyde (2.44 g, 20 mmol) and 2-trifluoroacetophenone (3.95 g, 21 mmol) are dissolved in 20 ml of MeOH and the mixture is treated at room temperature with 3 ml of 40% aq. KOH. After 1 h, it is poured onto water and the solid which is deposited is filtered off with suction. After washing with ether and drying under reduced pressure, 3.56 g (61% yield) of 1-(2'-trifluoromethylphenyl)-3-(2-amine-3-pyridyl)-2-propen-1-one are obtained. M.p. 161°–164° C.

The compound obtained above (2.7 g) is dissolved in glacial acetic acid (20 ml) and treated with conc. $H_2SO_4$ (2 ml) and the mixture is refluxed for 8 h. After cooling, it is neutralized with NaOH and extracted with ethyl acetate, and the crude product obtained is purified by chromatography on $SiO_2$ (cyclohexane/ethyl acetate 1:1). 1.95 g (77% yield) of the naphthyridine are obtained. M.p. 88°–91° C.

Example 5

2-(2'-Chlorophenyl)-6-methyl-7-phenyl-1,8-naphthyridine

2-Amino-5-methyl-6-phenylnicotinaldehyde (1.5 g, 7.1 mmol) and 2-chloroacetophenone (1.2 g, 7.7 mmol) are dissolved in 10 ml of MeOH, and the mixture is treated at room temperature with 2 ml of 40% KOH and stirred overnight at this temperature. The precipitate which is deposited is purified by chromatography ($SiO_2$, EtOAc/MeOH 9:1). 0.9 g (yield 38%) of the desired compound is obtained. M.p. 219°–222° C.

Example 6

2-(2'-Chlorophenyl)-4,6-dimethyl-7-phenyl-1,8-naphthyridine

2-Acetyl-2-amino-5-methyl-6-phenylpyridine (0.9 g, 3.9 mmol) and 2-chloroacetophenone (0.7 g, 4.6 mmol) are dissolved in 20 ml of MeOH and the mixture is treated with 2 ml of 40% KOH. After stirring at room temperature for 3 days, the precipitate which is deposited is filtered off with suction and purified bychromatography ($SiO_2$, cyclohexane/EtOAc 9:1). 0.4 g (yield 30%) of the desired compound is obtained. M.p. 151°–153° C.

Example 7

2-(2-Thiazolyl)-1,8-naphthyridine

2-Aminonicotinaldehyde (1.5 g, 12.3 mmol) and 2-acetylthiazole (1.64 g, 12.9 mmol) are dissolved in 12 ml of MeOH and the mixture is treated with 1.5 ml of 40% KOH. After 3 h, the reaction is complete and the mixture is poured onto water. The solid which is deposited is filtered off with suction, washed and dried. 1.22 g (yield 46%) of the desired product are obtained. M.p. 160°–165° C.

Other compounds which were obtained in a similar manner can be inferred from the following Tables.

TABLE 1

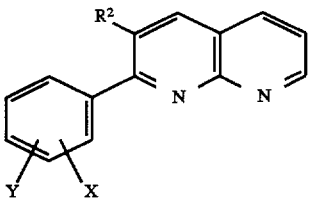

| No. | X, Y | $R^2$ | M.p. |
|---|---|---|---|
| 1.1 | H, H | H | 113–115[a)] |
| 1.2 | 4-$CH_3$, H | H | 146–150[b)] |
| 1.3 | 4-Cl, H | H | 197–201[b)] |
| 1.4 | 4-$OCH_3$, H | H | 145–150[b)] |
| 1.5 | 3-Cl, H | H | 100–102 |
| 1.6 | 3-$CH_3$, H | H | 101–104 |
| 1.7 | 3-$CF_3$, H | H | 142–147[e)] |
| 1.8 | 3-$OCH_3$, H | H | 136–139 |
| 1.9 | 3,4-$Cl_2$, H | H | 199–202 |
| 1.10 | H, H | $CH_3$ | 107–111[e)] |
| 1.11 | 2-$CH_3$, H | H | 128–130 |
| 1.12 | 2-Cl, H | H | 137–140 |
| 1.13 | H, H | i-$C_3H_7$ | 165–167 |
| 1.14 | 2-$OCH_3$, H | H | 137–141[d)] |
| 1.15 | 2-F, H | H | 111–114 |
| 1.16 | H, H | Et | 123–125[e)] |
| 1.17 | H, H | 2-ethylhexyl | 75–78 |
| 1.18 | H, H | n-$C_3H_7$ | 59–64 |
| 1.19 | 4-F, H | H | 208–209 |
| 1.20 | 4-$CF_3$, H | H | 179 |
| 1.21 | 4-CN, H | H | 224–226 |
| 1.22 | 2-$NO_2$, H | H | 188–190 |
| 1.23 | 2-Br, H | H | 131–136 |
| 1.24 | 2-OH, H | H | 188–191[b)] |
| 1.25 | 2-OH, H | $CH_3$ | 117–119 |
| 1.26 | 2-$CH_3$, 5-t-$C_4H_9$ | $CH_3$ | 184–186 |
| 1.27 | 3-$CF_3$, H | H | 88–91 |
| 1.28 | 2,6-$Cl_2$ | H | 150–156 |
| 1.29 | 2-F, H | $CH_3$ | 65–70 |
| 1.30 | 2,6-$F_2$ | H | 100–103 |
| 1.31 | 2-$CF_3$, H | $CH_3$ | 214–219 |
| 1.32 | 2-F, 6-$CF_3$ | H | 118 |
| 1.33 | 2,6-$F_2$ | $CH_3$ | 74–77 |
| 1.34 | 3-$OCF_3$, H | H | 105–109 |
| 1.35 | 2-F, 4-$OCH_3$ | H | 126–129 |

TABLE 1-continued

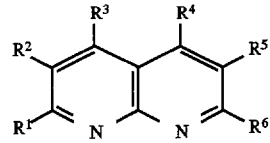

| No. | X, Y | R² | M.p. |
|---|---|---|---|
| 1.36 | 2,5-F₂ | H | 119–125 |
| 1.37 | 2,3-F₂ | CH₃ | 140–141 |
| 1.38 | 2,6-F₂ | C₂H₅ | 119–120 |
| 1.39 | 2,4-F₂ | H | 151 |
| 1.40 | 2-F, 3-CF₃ | CH₃ | 189–190 |
| 1.41 | 2-F, 3-CF₃ | H | 145–146 |
| 1.42 | 2,3-F₂ | H | 131 |
| 1.43 | 2,5-F₂ | CH₃ | 130 |
| 1.44 | 2,4-F₂ | CH₃ | 157–159 |
| 1.45 | 4-NO₂, H | H | >250 |
| 1.46 | 2-CH₃, H | CH₃ | 124 |
| 1.47 | 2-F, H | C₂H₅ | 91 |
| 1.48 | 2-CH₃, H | C₂H₅ | 128 |
| 1.49 | 2,3-Cl₂ | H | 190–192 |
| 1.50 | 2,4-Cl₂ | H | 169–174 |
| 1.51 | 2,5-Cl₂ | H | 139 |
| 1.52 | 2,3,4-Cl₃ | H | 178–181 |
| 1.53 | 2-CH₃, 4-CH₃ | H | 100–104 |
| 1.54 | 2-NH₂ | H | 200–206 |
| 1.55 | H,H | 3-pyridyl | 150 |
| 1.56 | H,H | SO₂-phenyl | 183–184 |
| 1.57 | H,H | C(O)-phenyl | 182–183[i)] |
| 1.58 | H,H | CO₂C₂H₅ | 106–112 |
| 1.59 | 2-Cl | CH₃ | 140–142 |
| 1.60 | 2-OCH₃ | CH₃ | 146–149 |
| 1.61 | 2-,3-,6-F₃ | H | 133–136 |
| 1.62 | 2-Cl | C₂H₅ | 135–136 |
| 1.63 | NHacetyl | H | 169–170 |
| 1.64 | 2-F | i-C₃H₇ | 141 |
| 1.65 | 2-CH₃ | i-C₃H₇ | 131 |
| 1.66 | 2-Cl, 5-NO₂ | H | 175–179 |
| 1.67 | 2-OC(O)C₆H₅ | H | 127 |
| 1.68 | 2-CH₃, 4-CH₃, 5-CH₃ | H | 98–106 |
| 1.69 | 2-OC(O)CH₃ | H | 120 |
| 1.70 | 2-CH₃, 4-CH₃, 6-CH₃ | H | 130–132 |
| 1.71 | 2-Cl | i-C₃H₇ | 132–133 |
| 1.72 | 2-F, 4-Cl, 5-F | H | 174–177 |
| 1.73 | 2-CH₃, 3-CH₃, 6-CH₃ | H | 133–134 |
| 1.74 | H, H | CN | 225–226 |
| 1.75 | H, H | CH₂OCH₃ | 94–97 |
| 1.76 | 2-C₂H₅ | CH₃ | 145–148 |

[a)–e), i)]compounds not according to the invention, see references at the end of the Tables

TABLE 2

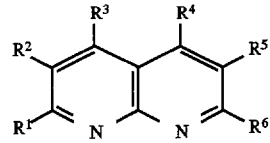

| No. | R¹ | R² | R³ | R⁴ | R⁵ | R⁶ | M.p. |
|---|---|---|---|---|---|---|---|
| 2.1 | phenyl | H | H | H | H | i-C₃H₇ | — |
| 2.2 | phenyl | CH₃ | H | H | H | i-C₃H₇ | — |
| 2.3 | 2-thienyl | H | H | H | H | i-C₃H₇ | 110–112 |
| 2.4 | 3-thienyl | H | H | H | H | i-C₃H₇ | 102–103 |
| 2.5 | 2-Cl-phenyl | H | H | H | H | i-C₃H₇ | 110–112 |

TABLE 2-continued

| No. | R¹ | R² | R³ | R⁴ | R⁵ | R⁶ | M.p. |
|---|---|---|---|---|---|---|---|
| 2.6 | phenyl | H | H | CH₃ | H | CH₃ | 152–154 |
| 2.7 | phenyl | CH₃ | H | CH₃ | H | CH₃ | 127–130 |
| 2.8 | 2-thienyl | H | H | CH₃ | H | CH₃ | 135–139 |
| 2.9 | 3-thienyl | H | H | CH₃ | H | CH₃ | 119–122 |
| 2.10 | 2-Cl-phenyl | H | H | CH₃ | H | CH₃ | 140–141 |
| 2.11 | phenyl | CH₃ | H | H | H | phenyl | 165–169 |
| 2.12 | phenyl | H | H | H | H | phenyl | 204–207[f)] |
| 2.13 | phenyl | CH₃ | H | CH₃ | H | phenyl | 193–195 |
| 2.14 | phenyl | CH₃ | H | H | CH₃ | phenyl | 240–248 |
| 2.15 | 2-thienyl | H | H | H | H | phenyl | 201–203 |
| 2.16 | 2-thienyl | H | H | H | CH₃ | phenyl | 257–258 |
| 2.17 | 2-thienyl | CH₃ | H | H | H | phenyl | 251–253 |
| 2.18 | 2-Cl-phenyl | H | H | H | CH₃ | phenyl | 219–222 |
| 2.19 | 2-thienyl | H | H | H | H | 2-thienyl | 224–225 |
| 2.20 | 2-Cl-phenyl | H | H | H | H | 2-thienyl | 204–205 |
| 2.21 | 2-thienyl | H | CH₃ | H | CH₃ | phenyl | 243–244 |
| 2.22 | 2-Cl-phenyl | H | CH₃ | H | CH₃ | phenyl | 151–153 |
| 2.23 | 2-F-phenyl | CH₃ | H | CH₃ | H | CH₃ | 131–132 |
| 2.24 | 2-F-phenyl | CH₃ | H | H | H | i-C₃H₇ | 102–103 |
| 2.25 | phenyl | C₂H₅ | H | CH₃ | H | CH₃ | 86–88 |
| 2.26 | phenyl | C₂H₅ | H | H | H | i-C₃H₇ | 124–125 |
| 2.27 | phenyl | H | H | CH₃ | CH₃ | H | 129–131 |
| 2.28 | phenyl | CH₃ | H | CH₃ | CH₃ | H | 175–177 |
| 2.29 | phenyl | C₂H₅ | H | H | CH₃ | H | 81–82 |
| 2.30 | 2-F-phenyl | CH₃ | H | CH₃ | CH₃ | H | 99–102 |
| 2.31 | phenyl | H | H | CH₃ | H | H | 110–111 |
| 2.32 | phenyl | CH₃ | H | CH₃ | H | H | 150–152 |
| 2.33 | phenyl | C₂H₅ | H | H | H | H | 98–100 |
| 2.34 | 2-F-phenyl | CH₃ | H | CH₃ | H | H | 148–149 |
| 2.35 | 2,6-F₂-phenyl | CH₃ | H | CH₃ | H | H | 179–180 |
| 2.36 | 2,6-F₂-phenyl | CH₃ | H | CH₃ | CH₃ | H | 152–153 |
| 2.37 | 2-F-phenyl | CH₃ | H | H | H | CH₃ | 137 |
| 2.38 | phenyl | CH₃ | H | H | H | CH₃ | 132 |
| 2.39 | phenyl | C₂H₅ | H | H | H | CH₃ | 119–122 |
| 2.40 | 2,6-F₂-phenyl | CH₃ | H | H | H | CH₃ | 170 |
| 2.41 | phenyl | H | CH₃ | H | H | H | 117–119 |
| 2.42 | phenyl | H | H | CF₃ | H | CH₃ | 99–100 |
| 2.43 | 2-F-phenyl | CH₃ | CH₃ | H | H | H | 139–141 |
| 2.44 | 2-F-phenyl | CH₃ | H | CF₃ | H | CH₃ | 150–151 |
| 2.45 | 2,6-F₂-phenyl | CH₃ | H | CF₃ | H | CH₃ | 120–122 |
| 2.46 | 3-pyridyl | phenyl | H | H | H | H | 150 |
| 2.47 | (2 amino)-3-pyridyl | H | CH₃ | H | H | H | 224–227 |

[f)]compounds not according to the invention, see references at the end of the Tables

TABLE 3

![structure with R² and R¹ on naphthyridine]

| No. | R¹ | R² | M.p. |
|---|---|---|---|
| 3.1 | 2-thienyl | H | 114–119[b] |
| 3.2 | 2-pyridyl | H | 147 |
| 3.3 | 3-thienyl | H | 101–108 |
| 3.4 | 2-thienyl | CH₃ | 101–103 |
| 3.5 | 2-(5-chlorothienyl) | H | 212–214 |
| 3.6 | 2-furanyl | H | 137–140[b] |
| 3.7 | 4-pyridyl | H | 169–171[b] |
| 3.8 | 3-pyridyl | H | 144 |
| 3.9 | N-methyl-2-pyrrolyl | H | 115–119 |
| 3.10 | 2-(3-methylthienyl) | H | 97–103 |
| 3.11 | 2-thiazolyl | H | 160–165 |
| 3.12 | 5-(2,4-dimethylthiazolyl) | H | 130–132 |
| 3.13 | 3-(2,5-dimethyl)thienyl | H | 80–83 |
| 3.14 | 2-naphthyl | H | 133–136[b] |

TABLE 4

| No. | M.p. |
|---|---|
| 4.1 | 76–88[g] |
| 4.2 | 201–202[h] |
| 4.3 | 134–137[g] |
| 4.4 | 201–203[g] |

[b],[g],[h] compounds not according to the invention, see references at the end of the Tables

References for Tables 1–4 a) E. M. Hawes, D. G. Wibberley, J. Chem. Soc.(C) 1967, 1564 b) K. V. Reddy et al., J. Ind. Chem. Soc. 1986, 443 c) T. Higashino et al., Chem. Pharm. Bull 1978, 26, 3242 d) Yakugaku Zasshi 1979, 99, 451–7 (CA 92(19): 163866a)

e) D. K. Garecki, E. M. Hawes, J. Med. Chem. 1977, 20(1), 124 f) J. P. Sauvage et al., Tetrahedron Lett. 1982, 23, 5291 g) R. P. Thummel et al., J. Heterocycl. Chem. 1986, 25, 689 h) E. J. S. Reddy et al., Natl. Acad. Sci. Lett. (India) 1985, 8, 19 (CA 103: 51079k)

i) G. Rama Rao et al., Ind. J. Chem. 1988, 27B, 200.

Use Examples

It was possible to show the herbicidal action of the naphthyridines of the formula I by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth and then covered with transparent plastic hoods until the plants had taken root. This covering causes a uniform germination of the test plants if this has not been adversely affected by the active compounds. The application rate for pre-emergence application was 2.0 kg/ha of a.s.

For the purpose of post-emergence treatment, the test plants were first raised to a height of growth of from 3 to 15 cm, depending on growth form, and only then treated with the active compounds suspended or emulsified in water. For this, the test plants were either sown directly and raised in the same containers or they were first raised separately as seedlings and transplanted into the experimental containers a few days before treatment. The application rate for post-emergence application was 2.0 or 1.0 kg/ha of a.s.

The plants were kept species-specifically at 10°–25° C. or 20°–35° C. The test period extended over 2 to 4 weeks. During this time, the plants were tended and their reaction to the individual treatments was assessed.

The herbicidal action was assessed on a scale from 0 to 100. 100 here means no emergence of the plants or complete destruction of at least the above-ground parts and 0 means no damage or normal course of growth.

The growth-regulating action was determined by length measurement. At the end of the test, the heights of growth of the treated plants were measured and related to the height of growth of untreated plants.

The plants used in the greenhouse tests were made up of the following species:

| Botanical name | Common name |
|---|---|
| *Alopecurus myosuroides* | blackgrass |
| *Amaranthus retroflexus* | redroot pigweed |
| *Avena fatua* | wild oat |
| *Chenopodium album* | lambsquarters (goosefoot) |
| *Echinochloa crus-galli* | barnyardgrass |
| *Ipomoea spp.* | morningglory |
| *Setaria faberii* | giant foxtail |
| *Setaria viridis* | green foxtail |

The results showed a very good herbicidal action of the compounds Nos. 1.11, 1.12, 1.29 and 1.16 according to the invention.

We claim:
1. A substituted naphthyridine of the formula I

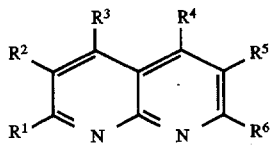

where the substituents have the following meanings:
$R^1$ is
- (c) phenyl substituted by one to four substituents selected from the group consisting of $C_1$–$C_8$-alkyl, $C_2$–$C_8$-alkenyl, $C_2$–$C_8$-alkynyl, $C_3$–$C_8$-cycloalkyl, phenyl, $C_1$–$C_5$-alkoxy, $C_1$–$C_5$-thioalkyl, a five- or six-membered saturated heterocycle, a five- or six-membered aromatic heterocycle, it being a five- or six-membered aromatic heterocycle, it being possible for all the abovementioned substituents in each case to be additionally mono- to trisubstituted themselves, hydroxyl, an $OC(O)R^{14}$ group, amino, an $NR^{15}R^{16}$ group, halogen, cyano, nitro, carboxyl, an $R^7SO_2$— group, —$C(O)R^8$, —$C(Y)R^9$, Y being oxygen or an $NR^{13}$ group, or —$C(VR^{10}WR^{11})R^{12}$, V and W independently of one another being O or S;

$R^7$ is $C_1$–$C_8$-alkyl, $C_3$–$C_8$-cycloalkyl, $C_1$–$C_8$-haloalkyl, $C_1$–$C_5$-alkoxy, phenyl, naphthyl, aryl($C_1$–$C_6$)-alkyl, heteroaryl, hydroxyl, amino, $C_1$–$C_8$-monoalkyl- or $C_1$–$C_8$-dialkylamino, $C_5$–$C_8$-cycloalkylamino;

$R^8$ is hydroxyl, amino, $C_1$–$C_8$-monoalkyl- or $C_1$–$C_8$-dialkylamino, $C_5$–$C_8$-cycloalkylamino, $C_1$–$C_6$-alkylthio, $C_1$–$C_8$-alkoxy;

$R^9$ hydrogen, $C_1$–$C_8$-alkyl, $C_3$–$C_8$-cycloalkyl, $C_{1-C8}$-haloalkyl, $C_1$–$C_4$-alkoxy($C_1$–$C_6$)-alkyl, $C_1$–$C_8$-aminoalkyl, phenyl, aryl($C_1$–$C_6$)-alkyl, heteroaryl;

$R^{10}$ and $R^{11}$ are $C_1$–$C_8$-alkyl, $C_1$–$C_6$-haloalkyl or $C_1$–$C_4$-alkoxy($C_1$–$C_6$)-alkyl, or $R^{10}$ and $R^{11}$ together form a di-, tri- or tetramethylene chain which is unsubstituted or substituted by one or two $C_1$–$C_8$-alkyl, $C_1$–$C_6$-haloalkyl, $C_1$–$C_4$-alkoxy($C_1$–$C_6$)-alkyl groups or by an oxo group;

$R^{12}$ is hydrogen, $C_1$–$C_8$-alkyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, phenyl, aryl($C_1$–$C_6$)-alkyl, heteroaryl;

$R^{13}$ is $C_1$–$C_8$-alkyl, $C_2$–$C_8$-alkenyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, phenyl, aryl ($C_1$–$C_6$)-alkyl, heteroaryl, hydroxyl, unsubstituted or substituted $C_6$–$C_{10}$-aryloxy, unsubstituted or substituted $C_1$–$C_8$alkoxy, amino, $C_1$–$C_8$-monoalkyl- or $C_1$–$C_8$-dialkylamino, $C_5$–$C_8$-cycloalkylamino, unsubstituted or substituted $C_6$–$C_{10}$-arylamino;

$R^{14}$ is $C_1$–$C_5$-alkyl, unsubstituted or substituted phenyl, $C_1$–$C_5$-alkoxy, $C_1$–$C_5$-haloalkoxy, benzyloxy, amino, alkylamino, dialkylamino, a saturated five- or six-membered heterocycle bonded via N, which can additionally contain a further heteroatom N or O;

$R^{15}$ is hydrogen, $C_1$–$C_5$-alkyl, unsubstituted or substituted phenyl;

$R^{16}$ is hydrogen, $C_1$–$C_5$-alkyl, unsubstituted or substituted phenyl, a —C(O)$R^{14}$ group or $R^{16}$ together with $R^{15}$ forms a four- or five-membered methylene chain which in turn can be substituted by one or two methyl groups and in which one methylene group can be replaced by oxygen;

$R^2$–$R^6$ are hydrogen, $C_1$–$C_8$-alkyl, $C_2$–$C_8$-alkenyl, $C_3$–$C_8$-cycloalkyl, $C_{C8}$-haloalkyl, $C_1$–$C_4$-alkoxy ($C_1$–$C_6$)-alkyl, $C_1$–$C_8$-aminoalkyl, unsubstituted or substituted phenyl, benzyl, unsubstituted or substituted five- or six-membered heteroaryl linked via a carbon, cyano, nitro, carboxyl, sulfonylmethyl, $C_1$–$C_4$-alkoxycarbonyl, carbamoyl, $C_1$–$C_8$-alkylcarbamoyl, dialkylcarbamoyl, $C_1$–$C_4$-alkanoyl, benzoyl or $R^4$ and $R^5$ or $R^5$ and $R^6$ together form a $CH_2$—$(CH_2)_n$—$CH_2$ chain where n=1 to 3 or an unfused aromatic ring;

with the proviso that compounds having the following substituent combinations are excluded:

xv) if $R^2$–$R^6$=hydrogen,
$R^1$ is not 4-chloro-phenyl, 4-bromophenyl, 4-nitrophenyl, 4-hydroxyphenyl, 4-methoxyphenyl, 4-methylphenyl, p-biphenyl, 2-hydroxy-4-chlorophenyl, 3-nitrophenyl, 3-trifluoro-methylphenyl, 2-hydroxyphenyl, 2-methoxyphenyl, 2hydroxy-5-nitrophenyl, 2-hydroxy-5-methylphenyl; and if $R^3$ is carboxy and $R^2$ and $R^4$–$R^6$ are hydrogen, $R^1$ is not o-hydroxyphenyl, p-methoxyphenyl or p-dimethylaminophenyl.

2. A naphthyridine of the formula I as claimed in claim 1, where the substituents $R^2$ to $R^6$ have the meanings mentioned in claim 1 and $R^1$ is defined as follows:

$R^1$ is phenyl substituted by one to four substituents selected from the group consisting of $C_1$–$C_8$-alkyl, $C_2$–$C_8$-alkenyl, $C_2$–$C_8$-alkynyl, $C_3$–$C_8$-cycloalkyl, phenyl, $C_1$–$C_5$-alkoxy, $C_1$–$C_5$-thioalkyl, a five- or six-membered saturated heterocycle, a five- or six-membered aromatic heterocycle, it being possible for all the abovementioned substituents in each case to be additionally mono- to trisubstituted themselves, hydroxyl, an $OC(O)R^{14}$ group, amino, an $NR^{15}R^{16}$ group, halogen, cyano, nitro, carboxyl, an $R^7SO_2$— group, —$C(O)R^9$, —$C(Y)R^9$, Y being oxygen or an $NR^{15}$ group, or —$C(VR^{10}WR^{11})R^{12}$, V and W independently of one another being O or S;

$R^7$ is $C_1$–$C_8$-alkyl, $C_3$–$C_8$-cycloalkyl, $C_1$–$C_8$-haloalkyl, $C_1$–$C_5$-alkoxy, phenyl, naphthyl, aryl($C_1$–$C_6$)-alkyl, heteroaryl, hydroxyl, amino, $C_1$–$C_8$-monoalkyl- or $C_1$–$C_8$-dialkylamino, $C_5$–$C_8$-cycloalkylamino;

$R^8$ is hydroxyl, amino, $C_1$–$C_8$-monoalkyl- or $C_1$–$C_8$-dialkylamino, $C_5$–$C_8$-cycloalkylamino, $C_1$–$C_6$-alkylthio, $C_1$–$C_8$-alkoxy;

$R^9$ is hydrogen, $C_1$–$C_8$-alkyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, phenyl, aryl($C_1$–$C_6$)-alkyl, heteroaryl;

$R^{10}$ and $R^{11}$ are $C_1$–$C_8$-alkyl, $C_1$–$C_6$-haloalkyl or $C_1$–$C_4$-alkoxy ($C_1$–$C_6$)-alkyl, or $R^{10}$ and $R^{11}$ together form a di-, tri- or tetramethylene chain which is unsubstituted or substituted by one or two $C_1$–$C_8$-alkyl, $C_1$–$C_6$-haloalkyl, $C_1$–$C_4$-alkoxy($C_1$–$C_6$)-alkyl groups or by an oxo group;

$R^{12}$ hydrogen, $C_1$–$C_8$-alkyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, phenyl, aryl ($C_1$–$C_6$)-alkyl, heteroaryl;

$R^{13}$ is $C_1$–$C_8$-alkyl, $C_2$–$C_8$-alkenyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, phenyl, aryl($C_1$–$C_6$)-alkyl, heteroaryl, hydroxyl, unsubstituted or substituted $C_6$–$C_{10}$-aryloxy, unsubstituted or substituted $C_1$–$C_8$-alkoxy, amino, $C_1$–$C_8$-monoalkyl- or $C_1$–$C_8$-dialkylamino, $C_5$–$C_8$-cycloalkylamino, unsubstituted or substituted $C_6$–$C_{10}$-arylamino;

$R^{14}$ is $C_1$–$C_5$-alkyl, unsubstituted or substituted phenyl, $C_1$–$C_5$-alkoxy, $C_1$–$C_5$-haloalkoxy, benzyloxy, amino, alkylamino, dialkylamino, a saturated five- or six-membered heterocycle bonded via N, which can additionally contain a further heteroatom N or O;

$R^{15}$ is hydrogen, $C_1$–$C_5$-alkyl, unsubstituted or substituted phenyl;

$R^{16}$ is hydrogen, $C_1$–$C_5$-alkyl, unsubstituted or substituted phenyl, a —C(O)$R^{14}$ group or $R^{16}$ together with $R^{15}$ forms a four- or five-membered methylene chain which in turn can be substituted by one or two methyl groups and in which one methylene group can be replaced by oxygen.

3. A naphthyridine as defined in claim 2, $R^1$ being a phenyl radical which is substituted in the ortho position.

4. A naphthyridine as defined in claim 3, the ortho substituent on the phenyl ring having the following meanings: $C_1$–$C_5$-alkyl, $C_3$–$C_6$-cycloalkyl, $C_1$–$C_4$-alkoxy, chlorine or fluorine.

5. A naphthyridine of the formula I as claimed in claim 1, where the substituents have the following meanings:

$R^1$ is phenyl substituted by one to four substituents selected from the group consisting of $C_1$–$C_8$-alkyl, $C_2$–$C_8$-alkenyl, $C_2$–$C_8$-alkynyl, $C_3$–$C_8$-cycloalkyl, phenyl, $C_1$–$C_5$-alkoxy, $C_1$–$C_5$-thioalkyl, a five- or six-membered saturated heterocycle, a five- or six-membered aromatic heterocycle, it being possible for all the abovementioned substituents in each case to be additionally mono- to trisubstituted themselves, hydroxyl, an OC(O)$R^{14}$ group, amino, an $NR^{15}R^{16}$ group, halogen, cyano, nitro, carboxyl, an $R^7SO_2$— group, —C(O)$R^8$, —C(Y)$R^9$, Y being oxygen or an $NR^{13}$ group, or —C(V$R^{10}$W$R^{11}$)$R^{12}$, V and W independently of one another being O or S;

$R^7$ is $C_1$–$C_8$-alkyl, $C_1$–$C_8$-haloalkyl, phenyl;

$R^8$ is $C_1$–$C_8$-monoalkyl- or $C_1$–$C_8$-dialkylamino, $C_5$–$C_8$-cycloalkylamino, $C_1$–$C_8$-alkoxy;

$R^9$ is hydrogen, $C_1$–$C_8$-alkyl, $C_3$–$C_8$-cycloalkyl, $C_1$–$C_8$-haloalkyl, phenyl, heteroaryl;

$R^{10}$ and $R^{11}$ are $C_1$–$C_8$-alkyl, or $R^{10}$ and $R^{11}$ together form a di-, tri- or tetramethylene chain which is unsubstituted or substituted by one or two $C_1$–$C_8$-alkyl, $C_1$–$C_6$-haloalkyl, $C_1$–$C_4$-alkoxy-($C_3$–$C_8$)-alkyl groups or an oxo group;

$R^{12}$ is hydrogen, $C_1$–$C_8$-alkyl, $C_3$–$C_8$-cycloalkyl, $C_1$–$C_8$-haloalkyl, phenyl, heteroaryl;

$R^{13}$ is $C_1$–$C_8$-alkyl, phenyl, aryl($C_1$–$C_6$)-alkyl, unsubstituted or substituted $C_6$–$C_{10}$-aryloxy, unsubstituted or substituted $C_1$–$C_8$-alkoxy;

$R^{14}$ is $C_1$–$C_8$-alkyl, unsubstituted or substituted phenyl, $C_1$–$C_5$-alkoxy, $C_1$–$C_5$-haloalkoxy, benzyloxy, amino, alkylamino, dialkylamino, a saturated five- or six-membered heterocycle bonded via N;

$R^{15}$ is hydrogen, $C_1$–$C_5$-alkyl, unsubstituted or substituted phenyl;

$R^{16}$ is hydrogen, $C_1$–$C_8$-alkyl, unsubstituted or substituted phenyl, a —C(O)$R^{14}$ group, or $R^{16}$ together with $R^{15}$ forms a four- or five-membered methylene chain which, in turn, can be substituted by one or two methyl groups and in which one methylene group can be replaced by oxygen;

$R^2$ is hydrogen, $C_1$–$C_8$-alkyl, $C_1$–$C_8$-haloalkyl, $C_3$–$C_8$-cycloalkyl, unsubstituted or substituted phenyl, benzyl;

and $R^3$–$R^6$ are hydrogen, $C_1$–$C_8$-alkyl, $C_1$–$C_8$-haloalkyl, $C_3$–$C_8$-cycloalkyl, unsubstituted or substituted phenyl, benzyl, unsubstituted or substituted five- or six-membered heteroaryl linked via a carbon, cyano, nitro, carboxyl, sulfonylmethyl, $C_1$–$C_4$-alkoxycarbonyl, carbamoyl, alkylcarbamoyl, dialkylcarbamoyl, $C_1$–$C_4$-alkanoyl or benzoyl.

6. A naphthyridine as defined in claim 4, wherein the ortho substituent is fluorine.

7. A naphthyridine as defined in claim 6, wherein $R^2$ to $R^6$ are each hydrogen.

8. A naphthyridine as defined in claim 6, wherein $R^2$ is $C_1$–$C_8$-alkyl and $R^3$ to $R^6$ are each hydrogen.

9. A naphthyridine as defined in claim 6, wherein $R^2$ is methyl and $R^3$ to $R^6$ are each hydrogen.

10. A herbicidal composition, containing at least one substituted naphthyridine of the formula I as defined in claim 1 and customary inert carriers.

11. A herbicidal composition, containing at least one substituted naphthyridine of the formula I as defined in claim 5 and customary inert carriers.

12. A method for controlling undesired plant growth, which comprises allowing a herbicidally active amount of a substituted naphthyridine of the formula I

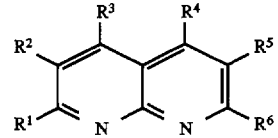

where the substituents have the following meanings:

$R^1$ is phenyl or phenyl substituted by one to four substituents selected from the group consisting of $C_1$–$C_8$-alkyl, $C_2$–$C_8$-alkenyl, $C_2$–$C_8$-alkynyl, $C_3$–$C_8$-cycloalkyl, phenyl, $C_1$–$C_5$-alkoxy, $C_1$–$C_5$-thioalkyl, a five- or six-membered saturated heterocycle, a five- or six-membered aromatic heterocycle, it being possible for all the abovementioned substituents in each case to be additionally mono- to trisubstituted themselves, hydroxyl, an OC(O)$R^{14}$ group, amino, an $NR^{15}R^{16}$ group, halogen, cyano, nitro, carboxyl, an $R^7SO_2$— group, —C(O)$R^8$, —C(Y)$R^9$, Y being oxygen or an $NR^{13}$ group, or —C(V$R^{10}$W$R^{12}$)$R^{12}$, V and W independently of one another being O or S;

$R^7$ is $C_1$–$C_8$-alkyl, $C_3$–$C_8$-cycloalkyl, $C_1$–$C_8$-haloalkyl, $C_1$–$C_5$-alkoxy, phenyl, naphthyl, aryl($C_1$–$C_6$)-alkyl, heteroaryl, hydroxyl, amino, $C_1$–$C_8$-monoalkyl- or $C_1$–$C_8$-dialkylamino, $C_5$–$C_8$-cycloalkylamino;

$R^8$ hydroxyl, amino, $C_1$–$C_8$-monoalkyl- or $C_1$–$C_8$-dialkylamino, $C_5$–$C_8$-cycloalkylamino, $C_1$–$C_6$-alkylthio, $C_1$–$C_8$-alkoxy;

$R^9$ is hydrogen, $C_1$–$C_8$-alkyl, $C_3$–$C_8$-cycloalkyl, $C_1$–$C_8$-haloalkyl, $C_1$–$C_4$-alkoxy($C_1$–$C_6$)-alkyl, $C_1$–$C_8$-aminoalkyl, phenyl, aryl($C_1$–$C_6$)-alkyl, heteroaryl;

$R^{10}$ and $R^{11}$ are $C_1$–$C_8$-alkyl, $C_1$–$C_6$-haloalkyl or $C_1$–$C_4$-alkoxy($C_1$–$C_6$)-alkyl, or $R^{10}$ and $R^{11}$ together form a di-, tri- or tetramethylene chain which is unsubstituted or substituted by one or two $C_1$–$C_8$-alkyl, $C_1$–$C_6$-haloalkyl, $C_1$–$C_4$-alkoxy($C_1$–$C_6$)-alkyl groups or by an oxo group;

$R^{12}$ is hydrogen, $C_1$–$C_8$-alkyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, phenyl, aryl($C_1$–$C_6$)-alkyl, heteroaryl;

$R^{13}$ is $C_1$–$C_8$-alkyl, $C_2$–$C_8$-alkenyl, $C_3$–$C_6$-cycloalkyl, $C_1$–$C_8$-haloalkyl, $C_1$–$C_4$-alkoxy($C_1$–$C_6$)-alkyl, $C_1$–$C_8$-aminoalkyl, phenyl, aryl($C_1$–$C_6$)-alkyl, heteroaryl, hydroxyl, unsubstituted or substituted $C_6$–$C_{10}$-aryloxy, unsubstituted or substituted $C_1$–$C_8$-alkoxy, amino, $C_5$–$C_8$-monoalkyl- or $C_1$–$C_8$-dialkylamino, $C_5$–$C_8$-cycloalkylamino, unsubstituted or substituted $C_6$–$C_{10}$-arylamino;

$R^{14}$ is $C_1$–$C_5$-alkyl, unsubstituted or substituted phenyl, $C_1$–$C_5$-alkoxy, $C_1$–$C_5$-haloalkoxy, benzyloxy, amino, alkylamino, dialkylamino, a saturated five- or six-membered heterocycle bonded via N, which can additionally contain a further heteroatom N or O;

$R^{15}$ is hydrogen, $C_1$–$C_5$-alkyl, unsubstituted or substituted phenyl;

$R^{16}$ is hydrogen, $C_1$–$C_5$-alkyl, unsubstituted or substituted phenyl, —C(O)$R^{14}$ group or $R^{16}$ together with $R^{15}$ forms a four-or five-membered methylene chain which in turn can be substituted by one or two methyl groups and in which one methylene group can be replaced by oxygen;

$R^2$–$R^6$ are hydrogen, $C_1$–$C_8$-alkyl, $C_2$–$C_8$-alkenyl, $C_3$–$C_8$-cycloalkyl, $C_1$–$C_8$-haloalkyl, $C_1$–$C_4$-alkoxy ($C_1$–$C_6$)-alkyl, $C_1$–$C_8$-aminoalkyl, unsubstituted or substituted phenyl, benzyl, unsubstituted or substituted five- or six-membered heteroaryl linked via a carbon, cyano, nitro, carboxyl, sulfonylmethyl, $C_1$–$C_4$-alkoxycarbonyl, carbamoyl, $C_1$–$C_8$-alkylcarbamoyl, dialkylcarbamoyl, $C_1$–$C_4$-alkanoyl, benzoyl or $R^4$ and $R^5$ or $R^5$ and $R^6$ together form a $CH_2$—$(CH_2)_n$—$CH_2$ chain where n=1 to 3 or an unfused aromatic ring;

to act on the plants and/or their habitat.

13. A method as defined in claim 12, wherein $R^1$ is a phenyl radical which is substituted in the ortho position, $R^2$ is hydrogen, fluorine or methyl and $R^3$ to $R^6$ are hydrogen.

14. A method as defined in claim 12, wherein $R^1$ is phenyl ortho substituted by fluorine and $R^2$ to $R^6$ are each hydrogen.

15. A method as defined in claim 12, wherein $R^1$ is phenyl ortho substituted by fluorine, $R^2$ is methyl and $R^3$ to $R^6$ are each hydrogen.

16. A naphthyridine as claimed in claim 3, the ortho substituent on the phenyl ring having the following meanings: $C_1$–$C_5$-alkyl, $C_3$–$C_6$-cycloalkyl, $C_1$–$C_4$-alkoxy, chlorine or fluorine.

* * * * *

UNITED STATES PATENT AND TRADEMARK OFFICE
CERTIFICATE OF CORRECTION

PATENT NO. : 5,723,413

DATED : March 3, 1998

INVENTOR(S) : BRATZ et al.

It is certified that error appears in the above-identified patent and that said Letters Patent is hereby corrected as shown below:

Column 29, claim 1, line 31, "alkylthlo" should be --alkylthio--.
Column 29, claim 1, line 32, "$R^9$ hydrogen" should be --$R^9$ is hydrogen--;
   "$C_3$-$C_8$-oycloalkyl" should be --$C_3$-$C_8$-cycloalkyl--; and
   "$C_1$-$C_8$-" should be -- $C_1$-$C_8$- --.
Column 29, claim 1, line 67, "$C_{C8}$" should be -- $C_1$-$C_8$- --.
Column 30, claim 1, line 17, "2hydroxy" should be --2-hydroxy--.
Column 30, claim 2, line 35, "$R^9$" should be --$R^8$--; line 36, "$NR^{15}$" should read --$NR^{13}$"
Column 30, claim 2, line 55, "$R^{12}$ hydrogen" should be --$R^{12}$ is hydrogen--.
Column 31, claim 5, line 65, "$C_3$-$C_8$-cycloalykl" should be --$C_3$-$C_8$-cycloalkyl--.
Column 32, claim 12, line 38, "-$C(VR^{10}WR^{12})R^{12}$" should be -- -$C(VR^{10}WR^{11})R^{12}$ --.
Column 32, claim 12, line 45, "$R^8$ hydroxyl" should be --$R^8$ is hydroxyl--.
Column 32, claim 12, line 60, "$R^{13}$ is C" should be --$R^{13}$ is C--.
Column 32, claim 12, line 60, "$C_3$-$C_6$-" should be -- $C_3$-$C_8$- --.
Column 32, claim 12, line 65, "$C_5$-$C_8$-" should be -- $C_1$-$C_8$- --.

Signed and Sealed this

Twenty-sixth Day of May, 1998

Attest:

BRUCE LEHMAN

Attesting Officer

Commissioner of Patents and Trademarks